(12) United States Patent
Cremillieux et al.

(10) Patent No.: US 10,517,962 B2
(45) Date of Patent: Dec. 31, 2019

(54) ULTRAFINE NANOPARTICLES AS MULTIMODAL CONTRAST AGENT

(71) Applicants: Universite Claude Bernard Lyon I, Villeurbanne (FR); Nano-H, Saint-Quentin-Fallavier (FR); Centre National de la Recherche Scientifique—CNRS, Paris (FR); Universite Joseph Fourier, Grenoble (FR)

(72) Inventors: Yannick Cremillieux, Bordeaux (FR); Andrea Bianchi, Bordeaux (FR); Sandrine Dufort, Grenoble (FR); Jean-Luc Coll, Le Pont de Claix (FR); Francois Lux, Lyons (FR); Olivier Tillement, Fontaines Saint Martin (FR)

(73) Assignees: Universite Claude Bernard Lyon I, Villeurbanne (FR); Nano-H, Saint Quentin Fallavier (FR); Universite Grenoble Alpes, Saint Martin d'Hères (FR); Universite de Bordeaux, Bordeaux (FR); Centre National de la Recherche Scientifique, Paris (FR)

(*) Notice: Subject to any disclaimer, the term of this patent is extended or adjusted under 35 U.S.C. 154(b) by 373 days.

(21) Appl. No.: 14/394,004

(22) PCT Filed: Apr. 12, 2013

(86) PCT No.: PCT/EP2013/057677
§ 371 (c)(1),
(2) Date: Oct. 10, 2014

(87) PCT Pub. No.: WO2013/153197
PCT Pub. Date: Oct. 17, 2013

(65) Prior Publication Data
US 2015/0050217 A1   Feb. 19, 2015

(30) Foreign Application Priority Data

Apr. 13, 2012 (FR) ..................... 12 53438

(51) Int. Cl.
| A61K 47/69 | (2017.01) |
| A61K 49/00 | (2006.01) |
| A61K 41/00 | (2006.01) |
| A61K 49/10 | (2006.01) |
| A61K 49/18 | (2006.01) |
| A61K 51/12 | (2006.01) |
| A61K 9/51  | (2006.01) |
| A61K 49/04 | (2006.01) |

(52) U.S. Cl.
CPC ........ *A61K 47/6923* (2017.08); *A61K 9/5146* (2013.01); *A61K 41/0038* (2013.01); *A61K 41/0057* (2013.01); *A61K 47/6929* (2017.08); *A61K 49/00* (2013.01); *A61K 49/0017* (2013.01); *A61K 49/0032* (2013.01); *A61K 49/04* (2013.01); *A61K 49/105* (2013.01); *A61K 49/108* (2013.01); *A61K 49/183* (2013.01); *A61K 49/1824* (2013.01); *A61K 51/1244* (2013.01)

(58) Field of Classification Search
None
See application file for complete search history.

(56) References Cited

U.S. PATENT DOCUMENTS

| 2011/0027375 A1* | 2/2011 | Tillement ............. A61K 9/0019 424/497 |
| 2011/0077506 A1* | 3/2011 | Driehuys ............... A61K 49/00 600/420 |
| 2013/0195766 A1  | 8/2013 | Lux et al. ................. 424/9.322 |

FOREIGN PATENT DOCUMENTS

| JP | 2008506636 | 3/2008 |
| WO | 2005116226 | 12/2005 |
| WO | WO 2007/124131 | 11/2007 |
| WO | WO 2011/135101 | 11/2011 |

OTHER PUBLICATIONS

Psimadas et al. Molecular nanomedicine towards cancer: 111In-labeled nanoparticles. 2012 J. Pharm. Sci. 101: 2271-2280. Published online Apr. 4, 2012.*
Dames et al. Targeted delivery of magnetic aerosol droplets to the lung. 2007 Nat. Nanotechnol. 2: 495-499. (Year: 2007).*
Lux et al. Ultrasmall rigid particles as multimodal probes for medical applications. 2011 Angew. Chem. Int. Ed. Engl. 50: 12299-12303. (Year: 2011).*
Laube BL. The expanding role of aerosols in systemic drug delivery, gene therapy, and vaccination. 2005 Respir. Care 50: 1161-1176. (Year: 2005).*
Fjälling et al. Systemic radionuclide therapy using indium-111-DTPA-D-Phe1-octreotide in midgut carcinoid syndrome. 1996 J. Nucl. Med. 37: 1519-1521. (Year: 1996).*
Mistleberger et al., "Luminescent Magnetic Particles: Structures, Syntheses, Multimodal Imaging and Analytical Applications," 2 *Bioanalytical Rev.* 61 (2010).

(Continued)

*Primary Examiner* — Jennifer A. Lamberski
(74) *Attorney, Agent, or Firm* — James C. Lydon

(57) ABSTRACT

The invention relates to a novel use of ultrafine nanoparticles, of use as a diagnostic, therapeutic or theranostic agent, characterized by their mode of administration via the airways. The invention is also directed toward the applications which follow from this novel mode of administration, in particular for imaging the lungs, and the diagnosis or prognosis of pathological pulmonary conditions. In the therapeutic field, the applications envisioned are those of radiosensitizing or radioactive agents for radiotherapy (and optionally curietherapy), or for neutron therapy, or of agents for PDT (photodynamic therapy), in particular for the treatment of lung tumors.

18 Claims, 5 Drawing Sheets

(56) References Cited

OTHER PUBLICATIONS

Hak Soo Choi et al., "Rapid Translocation of Nanoparticles From the Lund Airspaces of the Body," 28 *Nature Biotechnology* 1300 (2010).

Ozeki et al., "Nanoparticle-containing Microspheres Drug Delivery System (DDS) for Inhalation Therapy," 21 J. Aerosol Res. 10 (2006). Abstract only in English.

Cheow et al., "Preparations of Dry-Powder Therapeutic Nanoparticle Aerosols for Inhaled Drug Delivery," 25 Earozoru Kenkyu 155 (2010), 11 pages.

Reddy, A Question for Anyone Getting an MRI, Wall Street J., vol. CCLXX, No. 67, p. A11 (Sep. 19, 2017).

Bianchi et al., "Targeting and In Vivo Imaging of Non-Small-Cell Lung Cancer Using Nebulized Multimodal Contrast Agents," Proc. Nat'l.Acad.Sci. USA 2014; 111: 9247-9252; www.pnas.org/cgi/doi/10.1073/pnas.1402196111.

Bianchi et al., "Orotracheal Administration of Contrast Agents: A New Protocol for Brain Tumor Targeting," NMR Biomed. 2015; 28:738-746.

Dufort et al., "Nebulized Gadolinium-Based Nanoparticles: A Theranostic Approach for Lung Tumor Imaging and Radiosensitization," Small, 2015, 11:215-221.

\* cited by examiner

ULTRAFINE NANOPARTICLES AS MULTIMODAL CONTRAST AGENT

TECHNICAL FIELD

The invention relates to a novel use of ultrafine nanoparticles, as a diagnostic, therapeutic or theranostic agent, characterized by their mode of administration via the airways. The invention is also directed toward the applications which follow from this novel mode of administration, in particular for imaging the lungs, and the diagnosis or prognosis of pathological pulmonary conditions. In the therapeutic field, the applications envisioned are those of radiosensitizing or radioactive agents for radiotherapy (and optionally curietherapy), or for neutron therapy, or of agents for phototherapy or thermotherapy, in particular for the treatment of lung tumors.

TECHNOLOGICAL BACKGROUND

Despite considerable research efforts, cancer remains one of the major causes of death throughout the world (R. Siegel et al.: Cancer Statistics 2012, 2012, 62, 10-29). Among the various types of cancer, lung cancer constitutes the principal cause of cancer-associated death (J. S. Guthi et al., Molecular Pharmaceutics, 2009, 7, 32-40):
 there are 1.4 million deaths throughout the world each year,
 the 5-year survival rate is less than 15%.

The low survival of patients suffering from lung cancer is mainly due to the absence of tools for early diagnosis and for locally targeting therapeutic agents.

The use of nanoparticles as a contrast agent in medical imaging or as a therapeutic agent has been known for more than two decades. These nanoparticles in fact have many advantages compared with molecular compounds:
they allow a multimodal approach (M. Lewin et al., Nat. Biotechnol., 2000, 18, 410-414),
 detection is much improved owing to the greater number of active elements per particle; furthermore, in the case of MRI, the efficiency per $Gd^{3+}$ ion is also improved (P. Caravan, Chem. Soc. Rev., 2006, 35, 512-523/J. S. Ananta et al., Nat. Nano., 2010, 5, 815-821),
 it is possible to graft several molecules of a particular ligand per nanoparticle and/or to combine several types of ligands per nanoparticle in order to increase the affinity of the nanoparticles for certain tissues or cell types depending on the application envisioned (E. Garanger et al., Org. Biomol. Chem., 2006, 4, 1958-1964/Z.-H. Jin et al., Molecular Cancer, 2007, 6, 41),
 their nanometric scale confers on them novel and original properties that can be used for biomedical applications (E. Boisselier, D. Astruc, Chem. Soc. Rev., 2009, 38, 1759-1782/C. Xu, S. Sun, Dalton Trans., 2009, 5583-5591/P. Zrazheveskiy et al., Chem. Soc. Rev., 2010, 39, 4326-4354),
 they are rigid, and exhibit little interaction with the biological medium.

The multimodal approach consists in particular in using a set of nanoparticles each comprising several molecular contest agents. It thus makes it possible to combine not only various imaging techniques, but also various therapeutic techniques by grouping together several agents that are active in therapy, in the same nanoparticle. The agents that are active in imaging and the agents that are active in therapy can be identical to or different than one another.

This approach is particularly suitable for the development of medicament in theranostics. It is also possible in particular to add other imaging functions (luminescence, scintigraphy, etc.), therapeutic functions (release of active ingredients, radiosensitization, curietherapy, etc.) and also biological targeting functions for concentration of therapeutic agents in the zone of interest. This approach makes it possible in particular to envision imaging-guided therapy by accurately determining the behavior of the theranostic agent in the body by virtue of its biodistribution visualized by imaging. The theranositc agent can then be activated (by X-rays, γ-rays, neutrons or light, according to the type of agent) at the best moment (when the concentration is at a maximum in the zone to be treated and at a minimum in the healthy tissues).

Patent application WO 2009/053644 describes nanoparticles based on lanthanides (gadolinium in particular) and uses thereof as radiosensitizing agents. It discloses the use of organic molecules at the surface or in the coating of nanoparticles, so as in particular to improve biodistribution and to promote local overconcentrations in the tumor zones.

Patent application WO 2011/135102 describes ultrafine nanoparticles, with a mean diameter of less than 5 nm, comprising a functionalized polyorganosiloxane matrix and including metal complexes, for example of gadolinium, and where appropriate other contrast or radiosensitizing agents. These ultrafine nanoparticles have multimodal properties which are particularly advantageous in medical imaging and in cancer therapy. After an intravenous injection, an excellent biodistribution is noted along with rapid and complete renal elimination owing to their very small size, thereby limiting the risks of side effects or toxic effects (F. Lux et al., Ange. Chem. Int. Ed., 2011, 123, 12507-12511).

The lung is a unique organ in the sense that it can be targeted by a diagnostic or therapeutic agent either intravenously or via the airways. However, the administration of nanoparticles that can be used as a contrast agent is conventionally carried out by intravenous injection owing to the risks of long-term retention in the lungs (and therefore of associated tonicity) (J. Roller et al., Nanomedicine, 2011, 7, 753-762/R. Rossin et al., J. Nucl. Med., 2008, 49, 103-111).

In CT (computed tomography), the administration by inhalation of nanoparticles based on heavy elements (for example, gold (Cai, S. H. et al, Investigative Radiology, 2007, 42, 797-806) and iodinated compounds (Aillon, et al, Molecular Pharmaceutics, 2010, 7, 1274-1282)) has been described. In magnetic resonance imaging (MRI), only negative contrast agents (iron oxide-based nanoparticles (G. Huang et. al., Chem., 2009, 19, 6367-6372)) have been used via the airways because of their low toxicity and the ease with which they can be synthesized and functionalized. However, the use of a negative contrast agent is not optimal for imaging the lung, and the diagnosis might be improved by using positive contrast agents.

For fluorescence imaging, near-infrared (NIR) emission nanoparticles, such as quantum dots, have been used, but their inherent toxicity limits the possible future clinical applications. A. Zintcheko et al., Molecular Therapy, 2009, 17, 1849-1856/F-X. Blé et al, Magnetic Romance in Medicine 62:1164-1174 2009 describe the synthesis and the in vivo behavior of molecules capable of labeling mucus in order to study mucociliary clearance mechanisms. They show the advantage of using a fluorophore in the near-IR and also a contrast agent $T_1$ for their macromolecules. This approach does not make it possible to obtain a strong MRI signal (4 $Gd^{3+}$ for molecules of more than 10 kDa) or else it is necessary to dextran polymers of much higher molar mass (greater than 70 kDa). Furthermore, these polysaccharide-type polymers are biologically active and can interact with the glycoproteins of the mucus to bind to sites rich in hydrogen bonds. The contrast agent is eliminated by expectoration and does not make it possible to obtain an enhancement of the pulmonary tissues.

Thus, to the knowledge of the inventors, via administration, via the airways, of gadolinium-based nanoparticulate multimodal contrast agents has never been described for $T_1$ MRI imaging of the lungs. The inventors have now shown that an administration, via the airways, of a contrast agent in the form of ultrafine nanoparticles (with a mean diameter of less than 10 nm, or even less than 5 nm, for example between 1 and 5 nm) allows a contrast agent distribution that is particularly favorable for imaging of the lung or therapy for pathological pulmonary conditions and a satisfactory renal elimination, thus limiting the risks of toxicity that are inherent in structures of this type.

OBJECTIVES AND BRIEF DESCRIPTION OF THE INVENTION

The present invention aims to meet at least one of the following objectives:
(i) to propose novel modes of topical administration of multimodal contrast agents, in imaging (e.g. $T_1$ MRI, PET or SPECT scintigraphy, near-IR fluorescence, X-ray tomography), and which are weakly toxic;
(ii) to propose novel imaging methods enabling reliable detection of pathological pulmonary conditions, in particular lung tumors or bronchial remodeling associated with severe asthma, optionally coupled to a therapeutic act;
(iii) to propose novel diagnostic, therapeutic or theranostic agents for pathological pulmonary conditions, and in particular lung cancer or asthma, said agents having a strong potential in $T_1$ MRI combined with other imaging modes, an appropriate pulmonary distribution, a passage in the blood and efficient renal elimination;
(iv) to propose novel means of administering a prodrug or a contrast agent, requiring few devices and making it possible to reduce the doses to be injected by a route that is noninvasive, comfortable and nontoxic for the patient;
(v) to propose novel means for targeting non-pulmonary tumors, via a noninvasive administration, by virtue of the passage in the blood.

These objectives, among others, are achieved by the present invention which relates, in a first aspect, to nanoparticles for use as a therapeutic agent or as a contrast agent for medical imaging,
having a mean diameter of between 1 and 20 nm, preferably between 1 and 10 nm, and even more preferably between 2 and 5 nm or else between 1 and 5 nm,
comprising at least one contrast agent for medical imaging and/or one radiosensitizing or radioactive agent for radiotherapy, or an agent for neutron therapy, phototherapy or thermotherapy,
and characterized in that they are administered to humans or animals via the airways, in particular intranasally or intratracheally.

In one preferred embodiment, use is made of hybrid nanoparticles comprising:
a polyorganosiloxane (POS) matrix including, as contrast or radiosensitizing agent, rare earth cations $M^{n+}$, n being an integer between 2 and 4, optionally partly in the form of a metal oxide and/or oxyhydroxide, optionally associated with doping cations $D^{m+}$, m being an integer between 2 and 6, D preferably being a transition element or a rare earth metal;
a chelating agent grafted to the POS matrix via a covalent bond —Si—C—, in sufficient amount to be able to complex all $M^{n+}$ cations and, where appropriate, $D^{m+}$ cations; the chelating agent thus grafted preferably being in excess relative to the $M^{n+}$ cations and, where appropriate, $D^{m+}$ cations;
where appropriate, one or more targeting molecules, for the targeting of the nanoparticles, said targeting molecules being grafted to the POS matrix or to rise chelating agent.

In a second aspect, the invention is directed toward a method for noninvasive administration of hybrid nanoparticles as defined above, characterized in that the hybrid nanoparticles are administered to humans or animals via the airways in aerosol form.

In a third aspect, the invention is directed toward an aerosol for the administration of a contrast or therapeutic agent via the airways, containing nanoparticles as defined above and, where appropriate, a pharmaceutically acceptable vehicle, fluid or solvent. The invention relates to the pharmaceutical formulations suitable for these aerosols and to an aerosolization device containing same.

In a fourth aspect, the invention is directed toward a method for monitoring the therapeutic efficacy of a therapeutic treatment in humans or animals, said method comprising the following steps:
(i) at the initiation of the treatment, nanoparticles as defined above are administered to the patient, as a contrast agent, via the airways in the form of an aerosol,
(ii) the images are captured by an appropriate imaging technique in order to visualize the lesions,
(iii) steps (i) and (ii) are repeated during the treatment of the patient as many times as is necessary,
(iv) the therapeutic efficacy of the treatment is deduced by comparing the change in the lesions on the images during the treatment.

This method advantageously applies to the monitoring of the efficacy of an antitumor treatment, in particular directed against lung tumors, or else to the monitoring of the efficacy of a treatment against an inflammatory pulmonary ailment, such as asthma.

In a fifth aspect, the invention is directed toward nanoparticles for therapeutic uses against lung cancer, as a radiosensitizing, photosensitizing or radioactive agent, in radiotherapy, neutron therapy, curietherapy, dynamic phototherapy or thermotherapy.

DETAILED DESCRIPTION OF THE INVENTION

Nanoparticles Used in the Applications According to the Invention

The present invention follows from the surprising advantages, demonstrated by the inventors, of an administration via the airways of certain nanoparticles that can be used as a contrast agent, in particular in $T_1$ MRI. All the applications which follow therefrom are thus linked to the chemical and structural characteristics of these nanoparticles which are described hereinafter.

The invention in fact relates to nanoparticles, for use as a therapeutic agent or as a contrast agent for medical imaging, said nanoparticles having a mean diameter of between 1 and 20 nm, preferably between 1 and 10 nm, and even more preferably between 2 and 5 nm or else between 1 and 5 nm, and comprising at least one contrast agent for medical imaging and/or one radiosensitizing or radioactive agent for radiotherapy, or an agent for neutron therapy, phototherapy or thermotherapy, said particles being characterized in that they are administered to humans or animals via the airways, in particular intranasally or intratracheally.

According to the invention, nanoparticles with a very small diameter will advantageously be used. Nanoparticles with a mean diameter for example of between 1 and 10 nm, and even more preferably between 2 and 5 nm or between 1 and 5 nm, which allow an excellent distribution of these nanoparticles in the lungs (and therefore reliable detection of pathological pulmonary conditions), a passage in the blood and rapid renal elimination (and therefore low toxicity), will be selected. In one specific embodiment, said nanoparticles with a very small diameter, for example between 1 and 5 nm, are nanoparticles comprising at least one polyorganosiloxane matrix.

The size distribution of the nanoparticles is, for example, measured using a commercial particle sizer, such as a Malvern Zêtasizer Nano-S particle sizer based on PCS (Photon Correlation Spectroscopy). This distribution is characterized by a mean hydrodynamic diameter.

For the purposes of the invention, the term "mean diameter" is intended to mean the harmonic mean of the diameters of the particles. A method for measuring this parameter is also described in standard ISO 13321:1996.

For the purposes of the invention, the term "contrast agent" is intended to mean any product or composition used in medical imaging for the purpose of artificially increasing the contrast making it possible to visualize a particular anatomical structure (for example certain tissues or organs) or pathological anatomical structures (for example tumors) with respect to neighboring or non-pathological structures. The principle of how the contrast agent operates depends on the imaging technique used.

The exact structure of the contrast agent or of the radiosensitizing agent will be determined according to the desired application.

In one preferred variant, for applications in magnetic resonance imaging (MRI), the nanoparticles preferably contain rare earth metal cations, and even more preferably a lanthanide, having a magnetic behavior, such as Gd or Dy (or Eu for CEST), and representing at least 10% of all the metal cations present in the particles. The lanthanide-based, for example gadolinium-based, nanoparticles allow use as a $T_1$ MRI positive contrast agent, particularly suitable for imaging the lungs.

Thus, in one preferred embodiment, the nanoparticles each comprise a contrast or radiosensitizing agent chosen from a lanthanide and a lanthanide oxide and/or oxyhydroxide, the lanthanide preferably being chosen from Dy, Lu, Gd, Ho, Eu, Tb, Nd, Er and Yb, or mixtures thereof, and even more preferentially gadolinium.

Advantageously, and as is well known, it will be possible to combine the use of the nanoparticles in therapy and for an in vivo detection by MRI, enabling, for example, monitoring of a therapy. Preferably, only lanthanides, including at least 50% by weight of gadolinium (Gd), of dysprosium (Dy), of lutetium (Lu) or of holmium (Ho), or mixtures thereof, for example at least 50% by weight of gadolinium, will be chosen as radiosensitizing agent.

According to one variant, use will be made of nanoparticles in which the part containing lanthanides contains, at its periphery, lanthanides which cause an MRI signal, for example gadolinium, and at least one other lanthanide in its central part. Radiation-absorbing lanthanides with a high atomic number are therefore preferentially located at the center of the core of the nanoparticle.

According to another variant, it is known that a certain number of lanthanides exhibit effective cross sections for neutron capture coupled with a strongly energetic reaction allowing their use in treatments by neutron therapy for example against cancer. It will be possible to choose, as appropriate, in the therapy envisioned, a lanthanide which has an effective capture cross section sufficient for this purpose, so as to also allow treatment by neutron therapy. To this effect, the choice of gadolinium ($^{157}$Gd) proves to be particularly advantageous and lanthanides consisting of at least 50% by weight of gadolinium will be used as contrast agent.

In one preferred embodiment, the nanoparticles that can be used according to the invention are characterized in that they comprise at least one contrast agent for $T_1$ MRI imaging, and at least one other contrast agent suitable for one of the following imaging techniques:

(i) PET or SPECT scintigraphy,
(ii) fluorescence in the visible range or in the near-infrared range,
(iii) X-ray tomodensitometry.

Even more preferentially, the nanoparticles are chosen such that they have a relaxivity r1 per particle of between 50 and 5000 mM$^{-1}\cdot$s$^{-1}$ and/or a Gd weight ratio of at least 5%, for example between 5% and 50%.

For imaging by scintigraphy, the nanoparticles comprise a radioactive isotope that can be used in scintigraphy, and that is preferably chosen from the group consisting of the radioactive isotopes of In, Tc, Ga, Cu, Zr, Y or Lu, for example: $^{111}$In, $^{99m}$Tc, $^{68}$Ga, $^{64}$Cu, $^{89}$Zr, $^{90}$Y or $^{177}$Lu.

For fluorescence in the near-infrared range, a lanthanide chosen from Nd, Yb or Er may for example be used.

For fluorescence in the visible range, a lanthanide chosen from Eu or Tb can be used. These contrast or therapeutic agents are optionally protected with a coating of organic nature, for example a polyorganosiloxane matrix.

One embodiment thus relates to the hybrid nanoparticles of core-shell type. Nanoparticles of core-shell type, based on a core consisting of a rare earth oxide and of an optionally functionalized polyorganosiloxane matrix are in particular known (see in particular WO 2005/088314, WO 2009/053644).

The nanoparticles can be functionalized with molecules which allow targeting of the nanoparticles to specific tissues. The nanoparticle can also serve as a vector for the radiosensitizing agent and/or for the contrast agent, depending on the intended applications. Said agents can be coupled to the nanoparticle by covalent couplings, or trapped by non-covalent bonding, for example by encapsulation or hydrophilic/hydrophobic interaction or using a chelating agent.

In one preferred embodiment, use is made of hybrid nanoparticles comprising:

a polyorganosiloxane (POS) matrix including, as contrast or radiosensitizing agent, rare earth cations M$^{n+}$, n being an integer between 2 and 4, optionally partly in the form of a metal oxide and/or oxyhydroxide, optionally associated with doping cations D$^{m+}$, m being an integer between 2 and 6, D preferably being a rare earth metal other than M, an actinide and/or a transition element;

a chelating agent grafted to the POS matrix via a covalent bond —Si—C—, in sufficient amount able to complex all the M$^{n+}$ cations and, where appropriate, D$^{m+}$ cations; the chelating agent thus grafted preferably being in excess relative to the $M^{n+}$ cations and, where appropriate, $D^{m+}$ cations;

where appropriate, a targeting molecule, for the targeting of the nanoparticles, said targeting molecule being grafted to the POS matrix or to the chelating agent.

In the case of a structure of core-shell type, the POS matrix forms the superficial layer surrounding the metal cation-based core. Its thickness can range from 0.5 to 10 nm, and can represent from 25% to 75% of the total volume.

The POS matrix acts as protection for the core with respect to the external medium (in particular protection against hydrolysis) and it optimizes the properties of the contrast agents (luminescence, for example). It also allows the functionalization of the nanoparticle, via the grafting of chelating agents and of targeting molecules.

Advantageously, the chelating agent is chosen from the following products:

the products of the group of polyamino polycarboxylic acids and derivatives thereof, and even more preferentially in the subgroup comprising: DOTA, DTPA, EDTA, EGTA, BAPTA and NOTA, and mixtures thereof;

the products of the group comprising porphyrin, chlorine, 1,10-phenanthroline, bipyridine, terpyridine, cyclam, triazacyclononane, derivatives thereof and mixtures thereof;

and mixtures thereof.

If M is a lanthanide, the chelating agent is advantageously selected from those which have lanthanide-complexing properties, in particular those of which the complexation constant $\log(K_{C1})$ is greater than 15, preferentially 20. As preferred examples of lanthanide-complexing chelating agents, mention may be made of those comprising a unit of diethylenetriaminepentaacetic acid (DTPA), of 1,4,7,10-tetraazacyclododecane-1,4,7,10-tetraacetic acid (DOTA), or of 1,4,7-triazacyclononane-1,4,7-triacetic acid (NOTA), or derivatives thereof.

In addition, depending on the intended application, the nanoparticles are optionally doped with another rare earth or actinide metal cation, for example a lanthanide, or even two different lanthanides, at least one being chosen from Eu and Tb.

Among the actinides, in a variant suitable for applications in therapy linked to nuclear reactions, a radionuclide will for example be chosen from Ac, Th, Pa, Np, U and Pu.

Preferably, M and D are chosen from the following groups of elements: lanthanides, transition elements, actinides, and elements of columns Ib, IIa, IIb, Va, VIb, VIIb and VIII of the Periodic Table according to "The Merck Index—Eleventh edition";

preferably from the subgroups comprising:
the following lanthanides: Gd, Dy, Eu, Tb, Nd, Yb, Er, Ho, Lu;
Ib: Cu, Ag, Au;
IIa: Ca, Mg;
IIIa: Ga, In;
IIIb: Y;
Va: Bi;
VIb: Cr, Mo;
VIIb: Mn, Tc;
VII: Fe, Ru, Pt, Rh, Ir.

Gd and Dy are suitable, for example, for nanoparticles that are of use as a contrast agent in MRI.

Eu, Tb, Nd, Yb and Er are suitable, for example, for nanoparticles that are of use as a fluorescence agent.

Ho and Lu are suitable, for example, for nanoparticles that are of use as a curietherapy agent.

Lu, Yb, Gd and Ho are suitable, for example, for nanoparticles that are of use as a radiosensitizing agent.

According to one advantageous characteristic of the invention, the $M^{n+}$ and/or $D^{m+}$ cations are located at the surface of the nanoparticles. It follows from this that these cations are close to water molecules and can thus in particular have a significant $T_1$ contrast enhancement effect in MRI. This improvement in the performance levels of the nanoparticles used according to the invention is a control, among others, for the location of the $M^{n+}$ and/or $D^{m+}$ cations at the surface.

"Core-Free" Functionalized Ultrafine Nanoparticles

In one more particularly preferred embodiment, owing in particular to their very small size, the nanoparticles that can be used according to the invention are obtained from a precursor nanoparticle comprising:

a core comprising a rare earth metal oxide and/or oxyhydroxide (M), at least partly in cationic form $M^{n+}$, n being an integer between 2 and 4, optionally doped with a doping agent (D) present at least partly in cationic form $D^{m+}$, m being an integer between 2 and 6, preferably a transition element;

at least one coating layer comprising polyorganosiloxanes (POSs);

and, optionally, an overcoating comprising a chelating agent C1 capable of completing the $M^{n+}$ cations or a hydrophilic molecule capable of ensuring the suspending of the nanoparticles in an aqueous medium;

said precursor nanoparticle being subjected to complete or partial dissolution of the core M by means of a pH-modifying agent and/or of a chelating agent C2, identical to or different than C1, capable of completing all or part of the $M^{n+}$ and $D^{m+}$ cations, such that the mean diameter of the resulting particle is reduced to a value of between 1 and 20 nm, preferably between 1 and 10 nm, even more preferentially from 2 to 5 nm or else between 1 and 5 nm.

These nanoparticles obtained according to the mode described above do not comprise a core encapsulated by at least one coating. This results in observed sizes of between 3 and 5 nm. The term then used is ultrafine nanoparticles.

These "ultrafine" or "core-free" nanoparticles are optionally grafted to targeting molecules, and in particular molecules targeting lung tissues as described in the following paragraph.

Preferably, the chelating agents C1 and/or C2 are present in the nanoparticles in an amount such that all or part of the ions, in particular the $M^{n+}$ or even $D^{m+}$ cations, are not free but are complexed. Even better still, the weight percentage of the elements M and D involved in M-O-M or M-O-D or D-O-D or M-O—Si or D-O—Si bonds, relative to the total number of elements M and D, is less than or equal to, in an increasing order of preference, 10, 5, 2, 1, 0.5, $10^{-1}$, $10^{-2}$, $10^{-3}$.

The number of chelating agents C1 and/or C2 in the nanoparticles is greater than the number of remaining $M^{n+}$ cations and/or $D^{m+}$ cations, or even of other cations (e.g. $Ca^{++}$, $Mg^+$) optionally added in addition to the $M^{n+}$ and/or $D^{m+}$.

This percentage of M-O-M or M-O-D or D-O-D or M-O—Si or D-O—Si bonds (oxides) can be measured by means of the known techniques such as EXAFS, XPS, vibrational spectroscopy, transmission electron microscopy coupled to structural analyses, etc.

This measurement makes it possible to evaluate the number of specific bonds of the core. This measurement allows a quantitative measurement of the presence or absence of the core. It also makes it possible to evaluate the M or D species which could easily dissolve and find themselves in ionic form in solution.

The chelating agents C1 can be grafted at the surface of the polysiloxane particles or directly inserted into me POS matrix. A part or all of these chelating agents are intended for complexing $M^{n+}$ cations (e.g. gadolinium cations), or even $D^{m+}$ cations. Another part of these chelating agents can be used for the complexation of endogenous cations so as to ensure good compatibility with the biological media encountered.

One of the major advantages of the ultrafine nanoparticles according to the invention is that M and/or D can be an agent that is active in imaging (e.g. a contrast agent) and/or in therapy.

Indeed, $M/M^{n+}$ (e.g. of gadolinium) or even $D/D^{m+}$ exhibit notable properties for biological applications in imaging and/or in therapy, for instance magnetic, fluorescent, radioactive (element with a high atomic number) or radiosensitizing (X, gamma, beta, neutron) properties.

These nanoparticles can therefore be used as a contrast agent in imaging systems such as: MRI, SPECT scintigraphy, PET scintigraphy, fluorescence imaging, X-ray scans.

In addition to the chelating functionalization, these nanoparticles can be surface-modified (functionalization with hydrophilic compounds (PEG) and/or differently charged so as to adjust their biodistribution within the organism and/or to allow good cell labeling, in particular for monitoring cell therapies.

They can, for example, be surface-functionalized by grafting molecules which target pulmonary tissues, or, owing to their passage in the blood, by grafting molecules which target certain zones of interest of the organism, in particular rumor zones. In this way, the agent carried by these nanoparticles is concentrated in the zone of interest without having to very significantly increase the amounts injected, as is currently the case.

The functionalization can also be carried out using compounds comprising another active ingredient and/or luminescent compounds (fluorescein). This results in possibilities for therapeutic uses as a radiosensitizing agent in combination with radiotherapies or neutron therapies, as a radioactive agent for curietherapy treatments, as an agent for PDT (photodynamic therapy) or as an agent for vectorizing molecules with a therapeutic effect.

Another characteristic of these ultrafine nanoparticles is the maintaining of the rigid nature of the objects and of the overall geometry of the particles after injection. This strong three-dimensional rigidity is provided by the polysiloxane matrix, where the majority of the silicosis are bonded to 3 or 4 other silicon atoms by an oxygen bridge. The combination of this rigidity with their small size makes it possible to increase the relaxivity of these nanoparticles for the intermediate frequencies (20 to 60 MHz) compared with the commercial compounds (Gd-DOTA-based complexes for example), but also for frequencies above 100 MHz present in new-generation high-field MRIs.

This rigidity, not present in polymers, is also an asset for the vectorization and accessibility of the targeting molecules.

Moreover, it should be emphasized that the biocompatibility of these nanoparticles is not the least of their qualities.

Preferably, the nanoparticles according to the invention, and in particular according to the present embodiment, have a relaxivity $r_1$ per $M^{n+}$ ion greater than 5 mM$^{-1}$ (of $M^{n+}$ ion)·s$^{-1}$, preferentially 10 mM$^{-1}$ (of $M^{n+}$ ions)·s$^{-1}$, for a frequency of 20 MHz. For example, they have a relaxivity $r_1$ per nanoparticle of between 50 and 5000 mM$^{-1}$·s$^{-1}$. Even better still, these nanoparticles have a relaxivity $r_1$ per $M^{n+}$ ion at 60 MHz which is greater than or equal to the relaxivity $r_1$ per $M^{n+}$ ion at 20 MHz. The relaxivity $r_1$ considered here is a relaxivity per $M^{n+}$ (for example gadolinium) ion. $r_1$ is extracted from the following formula:

$$1/T_1 = [1/T_1]_{water} + r_1[M^{n+}].$$

In another variant, the nanoparticles have a weight ratio of T1 MRI contrast agent of lanthanide type, preferably of gadolinium, of greater than 5%, for example of between 5% and 50%.

Further details regarding these ultrafine nanoparticles, the processes for synthesizing them and their uses are described in patent application WO 2011/135101, which is incorporated by way of reference.

The Targeting Molecules

The targeting molecules are grafted at the surface of the nanoparticle and/or within the coating. Use may be made of conventional coupling with reactive groups that are present, optionally preceded by an activation step. The coupling reactions are known to those skilled in the art and will be chosen according to the structure of the superficial layer of the nanoparticle and to the functional groups of the targeting molecule. See, for example, "*Bioconjugate Techniques*", G. T. Hermanson, Academic Press, 1996, in "*Fluorescent and Luminescent Probes for Biological Activity*", Second Edition, W. T. Mason, ed. Academic Press, 1999. Preferred coupling methods are described later. Preferably, these targeting molecules are grated to the chelating agents of nanoparticles according to the "core-free" ultrafine nanoparticle variant as described in the previous section.

The targeting molecules will be chosen according to the application envisioned.

In one preferred embodiment, molecules suitable for the active targeting of tumors, in particular of lung tumors, will for example be chosen. By way of example of targeting molecules which can be grafted onto the nanoparticles, mention may be made of molecules containing the RGD tripeptide capable of recognizing $\alpha_v\beta_3$ integrin. Such peptides and derivatives thereof (in particular cyclic pentapeptide) are described in particular in WO 2004/026894.

It has recently been observed that $\alpha_v\beta_3$ integrin has a very specific expression profile in lung cancer. In healthy tissues, this heterodimer is undetectable (with the exception of osteoblasts), whereas it is expressed at approximately $10^5$ copies by cells essentially on the ventral face of the endothelial cells of capillaries undergoing neoformation or undergoing remodeling. The integrin is in fact involved in binding with the extracellular matrix so as to allow cell anchoring and mobility. Its accessibility via the blood stream is therefore moderate. As regards tumor cells and in particular lung cancer cells, $\alpha_v\beta_3$ integrin is more abundantly expressed on the tumor invasion front and also by the cells which escape from the rumor to form metastases. However, in addition, it has been noted that the tumor induces remodeling of the neighboring normal tissues, accompanied by overexpression of $\alpha_v\beta_3$ integrin on the surface of the normally negative cells. Thus, an administration of nanoparticles according to the invention, via the airways, for example by nebulization, said nanoparticles also comprising, grafted to their surface, molecules which target $\alpha_v\beta_3$ integrin, such as peptides containing the RGD motif, allows particularly effective targeting of lung tumors, in particular in comparison with a "conventional" intravenous administration.

It has also been noted by the inventors that the administration of the nanoparticles via the airways makes it possible to reach the blood stream, and therefore other tissues via the passage of the nanoparticles in the blood in the lungs, and/or the absorption of said nanoparticles by the cellular immune system. These nanoparticles can thus carry out a passive or active tumor targeting of non-pulmonary tumors, which are conventionally targeted by contrast agents via intravenous injection.

Thus, in some embodiments, molecules which target other organs, and in particular cancer tissues, will be chosen.

Targeting molecules suitable for targeting tumor tissues have been described, for example, in international publication WO 01/00621 and include quaternary ammonium derivatives, aptamers, polypeptides, antibodies, etc.

Hydrophilic Compounds

According to one variant of the invention, the nanoparticles can be functionalized at their surface with hydrophilic compounds chosen from the group of polyols, preferably from the subgroup comprising glycols, sugars and mixtures thereof; and dextrans, PEG and PPG being particularly preferred.

According to one alternative, these hydrophilic compounds can be chosen from those which have molar masses of less than 2000 g/mol, preferably less than 800 g/mol. Given hereinafter are examples of hydrophilic compounds, with their preferred molar mass (Mw):

poly(ethylene glycol)bis(carboxymethyl)ether (PEG), 250<Mw<2000 g·mol$^{-1}$;
polyoxyethylene bis(amine), 250<Mw<2000 g·mol$^{-1}$;
O-methyl-O'-succinyl polyethylene glycol, Mw of about 2000 g·mol$^{-1}$;
methoxypolyethylene glycol amine, Mw of about 750 g·mol$^{-1}$;
succinic and mercaptosuccinic acid;
sugars, in particular glucose and derivates thereof, for example dextrans;
hydrophilic amino acids or peptides (aspartic acid, glutamic acid, lysine, cysteine, serine, threonine, glycine, etc.);
and mixtures thereof.

More generally, the hydrophilic compounds advantageously comprise alcohol, carboxylic acid, amine, amide, ester, ether-oxide, sulfonate, phosphonate or phosphinate functions and will be bonded, preferably covalently, to at least 10% of the silicon atoms of the POS of the matrix.

Process for Obtaining the Nanoparticles According to the Invention

Generally, those skilled in the art will be able to easily produce nanoparticles used according to the invention. More specifically, the following elements will be noted:

for nanoparticles of core-shell type, based on a core of lanthanide oxide or oxyhydroxide, use will be made of a production process using an alcohol as solvent, as described for example in P. Perriat et al., *J. Coll. Int. Sci,* 2004, 273, 191; O. Tillement et al., *J. Am. Chem. Soc.,* 2007, 129, 5076 and P. Perriat et al., *J. Phys. Chem. C,* 2009, 113, 4038.

For the POS matrix, several techniques can be used, derived from those initiated by Stoeber (Stoeber, W; *J. Colloid Interf Sci* 1968, 26, 62). Use may also be made of the process used for coating as described in Louis et al. (Louis et al., 2005, *Chemistry of Materials,* 17, 1673-1682) or international application WO 2005/088314.

In practice, for the synthesis of ultrafine nanoparticles, a nanoparticle of core/shell type is formed with a lanthanide oxide core (via the modified polyol route) and a polysiloxane shell (via sol/gel); this object has, for example, a size of around 10 nm (preferentially 5 nanometers). A lanthanide oxide core of very small size (adjustable less than 10 nm) can thus be produced in an alcohol by means of one of the processes described in the following publications: P. Perriat et al., *J. Coll. Int. Sci,* 2004, 273, 191; O. Tillement et al., *J. Am. Chem. Soc.,* 2007, 129, 5076 and P. Perriat et al., *J. Phys. Chem. C,* 2009, 113, 4038.

These cores can be coated with a layer of polysiloxane according to, for example, a protocol described in the following publications: C. Louis et al., *Chem. Mat.,* 2005, 17, 1673 and O. Tillement et al., *J. Am. Chem. Soc.,* 2007, 129, 5076.

Chelating agents specific for the intended metal cations are grafted to the surface of the polysiloxane; it is also possible to insert a part thereof inside the layer, but the control of the formation of the polysiloxane is complex and simple external grafting gives, at these very small sizes, a sufficient proportion of grafting.

The nanoparticles are separated from the synthesis residues by means of a method of dialysis or of tangential filtration, on a membrane comprising pores of appropriate size.

The core is destroyed by dissolution (for example by modifying the pH or by introducing complexing molecules into the solution). This destruction of the core then allows a scattering of the polysiloxane layer (according to a mechanism of slow corrosion or collapse), which makes it possible to finally obtain a polysiloxane object with a complex morphology, the characteristic dimensions of which are of the order of magnitude of the thickness of the polysiloxane layer, i.e. much smaller than the objects produced up until now.

Removing the core thus makes it possible to decrease from a particle size of approximately 5 nanometers in diameter to a size of approximately 3 nanometers. Furthermore, this operation makes it possible to increase the number of M (e.g. gadolinium) per nm$^3$ in comparison with a theoretical polysiloxane nanoparticle of the same size but comprising M (e.g. gadolinium) only at the surface. The number of M for a nanoparticle size can be evaluated by virtue of the M/Si atomic ratio measured by EDX.

Targeting molecules can be grafted onto these nanoparticles for example using coupling by peptide bonding on an organic constituent of the nanoparticle, as described in Montalbetti, C. A. G. N, Falque B. *Tetrahedron* 2005, 61, 10827-10852.

Use may also be made of a coupling method using "click chemistry", Jewett, J. C.; Bertozzi, C. R. *Chem. Soc. Rev.* 2010, 39, 1272-1279, and involving groups of the type: —N$_3$, —CN or —C≡CH, or one of the following groups:

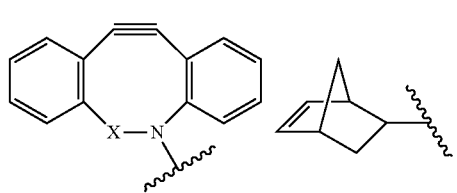

X = CH$_2$, CO

-continued

In one specific embodiment, the nanoparticle according to the invention comprises a chelating agent which has an acid function, for example DOTA. The acid function of the nanoparticle is activated for example using EDC/NHS (1-ethyl-3-(3-dimethylaminopropyl)carbodiimide/N-hydrosuccinimide) in the presence of an appropriate amount of targeting molecules. The nanoparticles thus grafted are then purified, for example by tangential filtration.

Mode of Administration of the Nanoparticles and Aerosol Containing the Nanoparticles According to one essential characteristic of the invention, the nanoparticles as defined above, and in particular the core-free ultrafine nanoparticles, are administered via the airways, in the form of an aerosol.

Thus, the invention relates to an aerosol for the administration of a contrast or therapeutic agent in humans or animals via the airways, said aerosol comprising, as contrast or therapeutic agent, nanoparticles as defined in the previous paragraphs, and more specifically core-free ultrafine nanoparticles, and, where appropriate, a pharmaceutically acceptable vehicle, fluid or solvent.

The term "airways" is intended to mean all of the airways of the respiratory tract, including the intranasal and intratracheal route, as opposed in particular to the other modes of administration of a medicament or of a contrast agent, consisting in particular of the oral or intravenous route. The objective is to reach the lungs by inhalation of the nanoparticles.

The term "aerosol" is intended to mean a semi-stable suspension of liquid droplets (containing the nanoparticles) or of solid particles dispersed in a support gas, for example air.

The aerosol is thus obtained by means of an appropriate device according to the parameters centered on the desired pharmacology or on the patient. The device enables, for example, the atomization of a predetermined volume of a liquid formulation containing a colloidal suspension of nanoparticles. According to the formulation and the dose desired, such devices include, without being limiting, an aerosol doser, a dry powder inhaler, a liquid-based inhaler, a (compressed air/jet) nebulizer, an ultrasonic nebulizer, a vibrating membrane/mesh nebulizer. For a detailed review of the usable inhalers (but which is nonlimiting), see in particular M. B. Dalovich et al., *Lancet*, 2001, 377, 1032-1045.

Thus, the invention also relates to a formulation of nanoparticles, as defined in the previous paragraphs, in particular of core-free ultrafine nanoparticles, said formulation being characterized in that it is suitable for administration by aerosolization. The formulation may be a liquid formulation containing the nanoparticles in the form of a stable colloidal suspension, for example in sterile water. Alternatively, it may be a dry matter resulting from the lyophilization of said liquid formulation containing the colloidal suspension. This dry matter is subsequently rehydrated in an appropriate volume of liquid before use.

The invention also relates to an inhaler containing a liquid or lyophilized formulation for aerosolization, as described above.

By way of example, for MRI imaging of the lungs, a formulation will be prepared which contains an appropriate dose of core-free ultrafine nanoparticles, based on gadoliniums, and optionally a contrast agent, said nanoparticles being in suspension in water. The administration of this formulation in aerosol form is carried out using a nebulizer, in the form of a saline solution, as described, for example, in the experimental section.

Medical Imaging Method

The invention also relates to a noninvasive method of medical imaging in humans or animals, comprising the following steps:
   (i) nanoparticles, as defined in the previous paragraphs, in particular core-free ultrafine nanoparticles, are administered as $T_1$ MRI contrast agent, via the airways, for example in the form of an aerosol,
   (ii) the MRI images are captured using an appropriate MRI sequence.

The imaging method thus comprises no invasive method and is particularly comfortable for the patient. In particular, it does not comprise an intravenous injection or contrast agent, the latter being administered only via the airways. It enables, where appropriate, a decrease in the dose administered, via a local administration (in the lungs) and a decrease in the side effects or toxic effects associated with the administration of contrast agents.

Step (i) has been described in the preceding paragraph.

For step (ii), the procedure is carried out conventionally using an MRI machine, choosing the appropriate MRI sequence according to the patient, the zone of interest to be studied and the type of image desired, as described for example in "*Comprendre l'IRM, manuel d'auto-apprentissage*"/"*Understanding MRI, self-learning manual*"/by Bruno Kastler, Daniel Vetler (publisher: Masson, 2011, ISBN: 9782294710445).

The nanoparticles used according to the invention are multimodal contrast agents. Thus, it is possible to combine, with a single administration, several imaging techniques and in particular $T_1$ MRI PET (e.g. $^{64}$Cu) or SPECT ($^{111}$In or $^{99m}$Tc) scintigraphy, fluorescence in the near-infrared range, optionally a radiosensitizing agent, a photosensitizing agent or an agent appropriate in radiotherapy, curietherapy, neutron therapy, phototherapy, etc.

In one particularly preferred mode, the method is applied to MRI imaging of the lungs, and in particular imaging of lung tumors. For lung tumor imaging, after administration of gadolinium-based core-free ultrafine nanoparticles a T1-weighted contrast will for example be sought with a short echo time in order to maximize the intensity of the pulmonary MRI signal. The MRI techniques used will take into account the specificities of pulmonary MRI, i.e. respiratory and cardiac movements, the low tissue density and the magnetic inhomogeneity of this organ ("*MRI of the Lung*", Hans Ulrich Kauczor, Ed. Springer, 2009, ISBN 9783540346180).

Owing to the administration in the lungs in the imaging methods according to the invention, an obvious application of said methods concerns the diagnosis of pathological pulmonary conditions, for example cancerous pathological conditions (lung tumors) and noncancerous pathological conditions, and in particular inflammatory pathological pulmonary conditions, including, for example, asthma, chronic obstructive pulmonary disease or chronic obstructive bronchopneumopathies.

The invention also relates to a method for monitoring the therapeutic efficacy of a therapeutic treatment in humans or animals, said method comprising the following steps:
   (i) at the initiation of the treatment, nanoparticles as defined above are administered to the patient as a contrast agent, via the airways in the form of an aerosol,
   (ii) the images are captured using an appropriate imaging technique in order to visualize the lesions,
   (iii) steps (i) and (ii) are repeated during the treatment of the subject, as many times as is necessary,
   (iv) the therapeutic efficacy of the treatment is deduced by comparing the change in the lesions during the treatment.

A particular application of this method relates to the monitoring of the therapeutic efficacy of a treatment in humans or animals, for example of an antitumor treatment, for example by chemotherapy, radiotherapy, curietherapy, phototherapy or thermotherapy, against lung tumors.

In one preferred embodiment, the invention is directed toward a method for monitoring the therapeutic efficacy of an antitumor treatment in humans or animals, in particular a treatment by chemotherapy, radiotherapy, curietherapy, phototherapy or thermotherapy, directed against lung tumors, said method comprising the following steps:
   (i) at the initiation of the treatment, nonoparticles, as defined in the preceding paragraphs, in particular core-free ultrafine nanoparticles, are administered to the patient suffering from cancer, as a contrast agent, via the airways, for example in the form of an aerosol,
   (ii) the images are captured using an appropriate imaging technique in order to detect the tumors,
   (iii) steps (i) and (ii) are repeated during the treatment of the patient with an antitumor agent,
   (iv) the therapeutic efficacy of the antitumor agent is deduced by comparing the images of the tumors obtained during the treatment.

Thus, it is possible to monitor the progression of tumors, in particular the size of the tumors over time, their number and their distribution, before, during and after the treatment of the patient. Nanoparticles enabling specific targeting of tumors as described above will naturally be chosen.

Advantageously in the methods described above, the nanoparticles can be used both as a contrast agent, owing to their multimodal property in imaging, for example as a $T_1$ MRI contrast agent and as a radiosensitizing, photosensitizing or radioactive agent for the treatment of tumors.

Thus, in the method described above, in one particular embodiment, the nanoparticles used as contrast agent are the same as those used as antitumor agent.

Another advantageous application according to the invention relates to the monitoring of therapeutic efficacy in pulmonary ailments, in particular inflammatory pathological pulmonary conditions such as asthma, chronic obstructive pulmonary disease or chronic obstructive bronchopneumopathies, or other pathological conditions, characterized by an increase on the part of the vessels in the bronchial wall (angiogenesis) and a hyperpermeability of the bronchial walls.

Therapeutic Applications by Aerosolization of the Nanoparticles

In combination with a radiosensitizing or radioactive agent for radiotherapy (and optionally curietherapy), or for neutron therapy, or with agents for PDT (photodynamic therapy), the nanoparticles administered in the airways are particularly useful for the treatment of tumors, and in particular for the treatment of lung tumors.

A subject of the invention is therefore also a pharmaceutical composition that can be used for the treatment of lung tumors, by chemotherapy, radiotherapy, curietherapy, phototherapy or thermotherapy, and that comprises nanoparticles as defined above, for example core-free ultrafine nanoparticles, as a radiosensitizing, photosensitizing or radioactive agent, optionally in combination with a pharmaceutically acceptable vehicle and/or other active ingredients or contrast agents that can be administered via the airways.

Method of Administration of a Contrast or Therapeutic Agent in the Blood Stream

The mode of administration via the airways enables a local administration in the lungs, but also passage of the nanoparticles in the systemic circulation. Thus, by coupling therapeutic molecules onto the nanoparticles (covalent or noncovalent coupling), the invention proposes the use of these nanoparticles as a vector for the administration via the airways, in the blood stream, of therapeutic molecules or of contrast agents. According to the mode of coupling of the therapeutic molecules, these vectors can be used as a prodrug with controlled, sustained or delayed release of the active ingredient.

The invention also relates to a method for treating a patient, comprising the administration, via the airways in the form of an aerosol, of a therapeutically effective dose of nanoparticles as defined in the preceding paragraphs, in particular of core-free ultrafine nanoparticles, as a therapeutic agent.

EXAMPLES

Chemical Products

Figure 1:
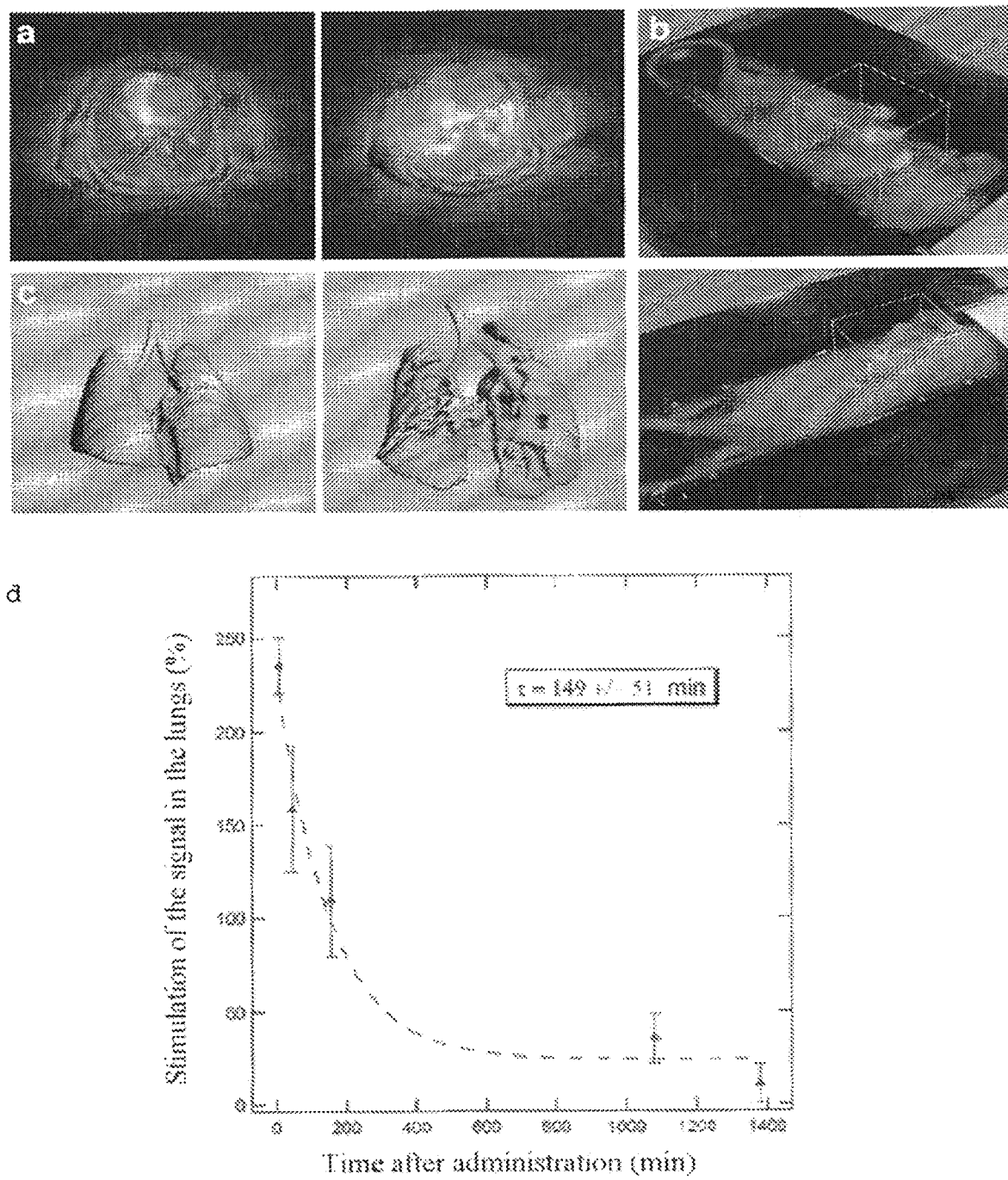
FIG. 1: a) MRI of the lungs in the mouse before (left) and 15 minutes after (right) the intratracheal administration of the SRP nanoparticles (40 microliters with a $Gd^{3+}$ ion concentration of 20 mM). A 183% enhancement of the intensity of the image is observed after administration of the nanoparticles, b) 3D fluorescence imaging of the mouse, 1 hour after nebulization (50 µl), in the lungs, of SRP nanoparticles grafted with the Cy5.5 fluorescent probe, c) 3D visualization of the lungs before (left) and after (right) nebulization of SRP nanoparticles (50 µl with a $Gd^{3+}$ ion concentration of 20 mM), obtained by X-ray microtomography (the "holes" correspond to the presence of nanoparticles), d) enhancement of the MRI signal in the lungs as a function of time (instillation of 40 µl of SRP solution with a $Gd^{3+}$ ion concentration of 20 mM), the time constant for detection of the nanoparticles before elimination via the kidneys is approximately two hours. All the nanoparticles used in these examples were synthesized according to the protocol described in example 1.
Figure 2:
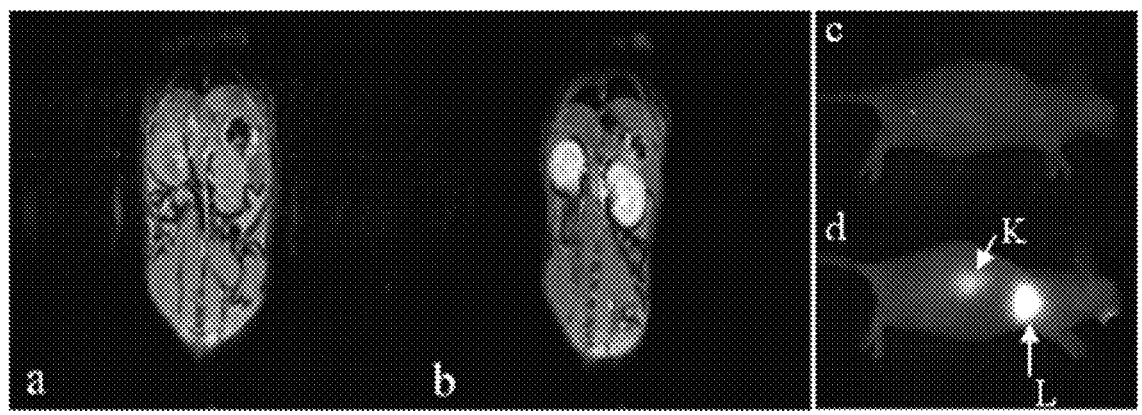
FIG. 2: images of the lungs of a mouse obtained before (a) by MRI and (c) by optical fluorescence imaging and 3 hours after the intratracheal administration of a solution of SRP nanoparticles obtained according to example 1 (coupled with a Cy 5.5 fluorophore for the fluorescence imaging) (40 microliters with a $Gd^{3+}$ ion concentration of 20 mM) (b) by MRI and (d) by fluorescence optical imaging. The images demonstrate the elimination of the nanoparticles via the kidneys (K: kidney, L: lung). No hepatic elimination is detected.
Figure 3:
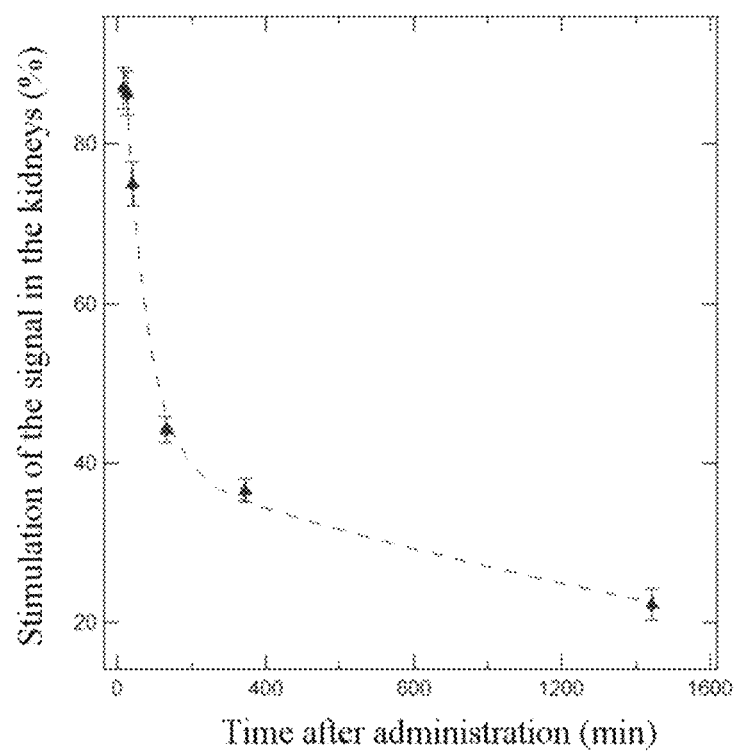
FIG. 3: evolution over time of the enhancement of the MRI signal in the kidneys following the intratracheal administration of a solution of contrast agent (50 mM $Gd^{3+}$) obtained according to example 1. The presence of nanoparticles in the kidneys is still detectable 24 hours after the administration of the solution.
Figure 4:
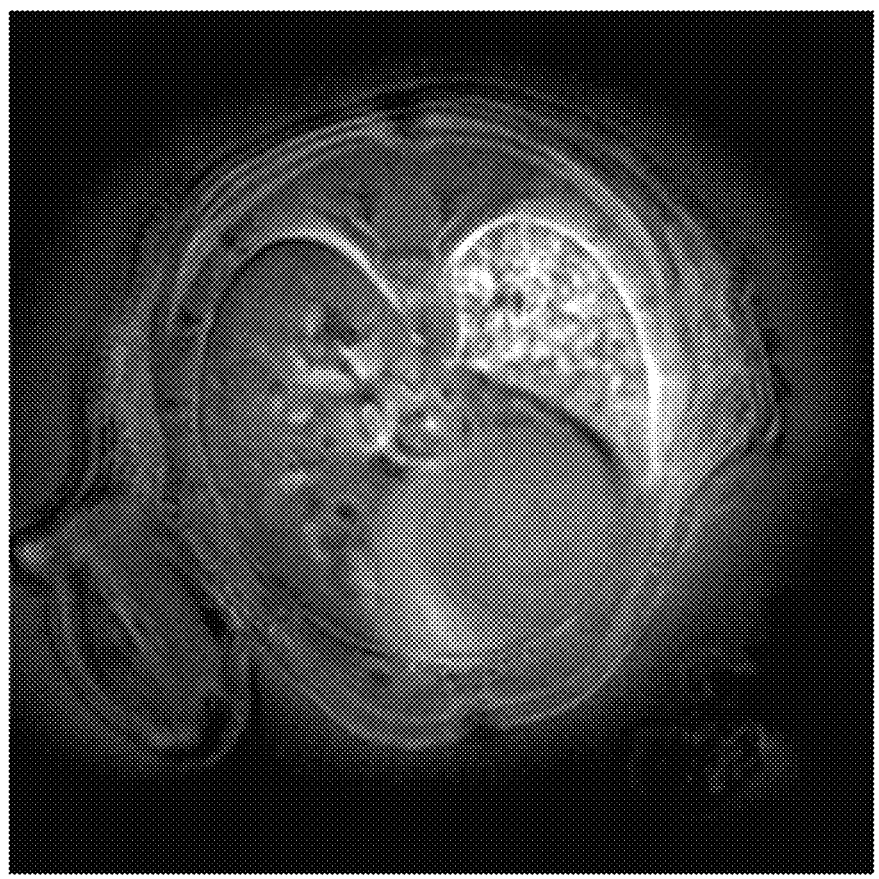
FIG. 4: high-resolution MRI image of the biodistribution of the contrast agent in the lungs of a mouse after selective administration of the solution (50 mM $Gd^{3+}$) in the left lung (on the right in the image). The nanoparticles used were obtained according to example 1. The main acquisition parameters are echo time 276 µs, section thickness 0.5 mm, field of view 2.5 cm, total acquisition time 4 minutes.

The gadolinium chloride hexahydrate ($[GdCl_3.6H_2O]$), 99%, the sodium hydroxide (NaOH, 99.99%), the tetraethoxysilane ($Si(OC_2H_5)_4$, TEOS, 98%), the aminopropyltriethoxysilane ($H_2N(CH_2)_3—Si(OC_2H_5)_3$, APTES, 99%), the triethylamine (TEA, 99.5%), the N-(3-dimethylaminopropyl)-N'-ethylcarbodiimide hydrochloride (EDC, >98.0%), the N-hydroxysuccinimide (NHS, >97.0%), the diethylenetriaminepentaacetic dianhydride (DTPADA) and the anhydrous dimethyl sulfoxide (DMSO, 99.5%) were obtained from Aldrich Chemicals (France). The Cy5.5 mono-NHS-ester was ordered from GE Healthcare. The diethylene glycol (DEG, 99%) comes form SDS Carlo Erba (France), while the acetone comes form Sodipro (France). The 1,4,7,10-tetraazacyclododecane-1-glutaric anhydride-4,7,10-triacetic acid (DOTAGA) was provided by CheMatech SAS. The cRGD cyclic tripeptide (Arg-Gly-Asp) comes form Genecust, Luxembourg. The 5-(4-carboxyphenyl)-10,15,20-triphenylchlorine (TPC) comes form Frontier Scientific (Logan, Utah).

Characterizations

The mean sizes of the nanoparticles indicated were measured by PCS (photon correlation spectroscopy) and correspond to their hydrodynamic diameter. These measurements were taken on a Zetasizer NanoS apparatus (the laser used for the PCS is a He—Ne 633 nm laser). The zetametry measurements were carried out on the same equipment, with the particles being diluted beforehand in a 0.01 M NaCl solution. The pH is adjusted a posteriori, Transmission electron microscopy (TEM) is carried out in order to obtain structural and morphological data on the samples. It was carried out using a JEOL 2010 microscope operating at 200 kV. The samples are prepared by deposition on a carbon grid. The relaxometry at 1.4 T (60 MHz) is measured on equipment of Bruker Minispec MQ60 type. The mass spectrometry is carried out using an LTQ spectrometer (Thermo Fisher Scientific, San Jose, Calif.). The elemental analyses were carried out at the analysis center of the CNRS [French National Center for Scientific Research] at Solaize by ICP-MS and made it possible to determine the C, N, Si and Gd contents with a minimum accuracy of 0.3%. The fluorescence analyses were obtained on a Varian Carry Eclipse spectrofluorometer. The lyophilization of the particles is carried on a Christ Alpha 1,2 lyophilizer.

Animals

The animals used for the proof of concept by MRI are 6-week-old Balb/c female mice weighing between 20 and 22 grams, these mice having been purchased from the Janvier breeding center (Le Genest, Saint-Isle, France). The animals used for the proof of concept by fluorescence imaging and X-ray tomography are 6-week-old NMRI nude female mice weighing approximately 25 grams, these mice having been purchased from the Janvier breeding center (Le Genest, Saint-Isle, France). Before the experiment, the mice acclimatized to their new environment in a temperature-controlled room for 1 week. The animal experiments are carried out while adhering to the instructions of INSERM (National Institute for Health and Medical Research) regarding animal welfare.

Imaging Tools

MRI

The MRI images were acquired on a Brucker Biospec 47/50 spectrometer with a field at 4.7 T (Brucker, Ettlingen, Germany), using an emitter/receiver coil with a diameter of less than 25 mm (Rapid Biomedical, Rimpar, Germany). The mice are placed on their stomach on a plastic cradle and kept anesthetized using a gas mask delivering 2% of isofluorane contained in an $N_2/O_2$ gas mixture (80:20). The body temperature is kept constant by virtue of a circulation of hot water and the respiratory cycle is constantly monitored.

For each animal, 6 axial sections 1 mm thick are acquired. The acquisition is carried out under free breathing without respiratory or cardiac synchronization using a multi-section 2D UTE (ultrashort echo time) sequence. The main parameters are echo time of 276 µs, repetition time of 84 ms, flip angle of 60°, field of view of 3 cm, total acquisition time of 1 minute.

Fluorescence Imaging

In order to carry out the 2D or 3D fluorescence imaging in vivo, the mice are anesthetized (isoflurane/oxygen: 3.5-4% for induction sod 1.5-2% for maintenance).

The 2D imaging system is composed of an excitation system composed of diodes emitting at a wavelength of 660 nm. The fluorescence images and also the "black and white"

images are taken with a CCD camera cooled to −80° C. (ORCA11-BT-512G, Hamamatsu, Massy, France), equipped with an RG 9 high-pass biter (Schott, Jena, Germany). The image acquisition and also the analysis are carried out with the Wasabi software (Hamamatsu, Massy, France). 24 h after the injection, the mice are sacrificed and the organs are imaged. A semi-quantification of the fluorescence of the organs is obtained by drawing regions of interest (ROIs) around the organs.

The florescence tomography is carried out using an fDOT 3D imaging system. The system is composed of a black box, an excitation light originating from a laser (690 nm, 26 mW, Powertechnology, St Nom La Bretche, France) and a CCD camera (ORCA ER, Hamamatsu) equipped with an RG 9 high-pass filter (Schott, Jena, Germany). The 3D mapping of the fluorescence in the mice is calculated by means of a reconstruction algorithm.

X-Ray Imaging

In order to carry out the X-ray imaging and the 2D or 3D fluorescence imaging in vivo, the mice are anesthetized (isoflurane/oxygen: 3.5-4% for induction and 1.5-2% for maintenance).

The X-ray tomography images are taken with the Scanco viva CT 40 (Scanco Medical, Inc., Bassersdorf, Switzerland) using an energy of 65 keV and an integration time of 200 ms. The 3D reconstructions of the lungs mark the presence of air in the lungs. The presence of the particles is therefore represented as a "hole" on the reconstructions, since the particles partly take the place of the air.

We also have a bed which fits in the X-ray scanner and the fluorescence tomography, allowing superimposition of the images and visualization of the colocalizations.

Example 1

Synthesis of Hybrid Gadolinium Nanoparticles of Gd—Si-DOTA: SRP (Small Rigid Platforms) Type The nanoparticles are obtained by means of a three-stage synthesis as described in WO 2011/135101. First of all, the oxide cores are synthesized in diethylene glycol before growth of the polysiloxane layer, followed by the covalent grafting of completing agents to the surface of the nanoparticle; the gadolinium oxide core dissolves when placed in water, thereby leading to fragmentation of the particles which makes it possible to obtain small particles of less than 5 nanometers composed only of polysiloxane, or organic species and of complexing agents useful in imaging.

The advantage of this top down approach is to make it possible to obtain very small particles which have multi-modal characteristics while at the same time having the advantage of being easy to eliminate via the kidneys.

Detailed Description of the Synthesis

Oxide Cores

A first solution is prepared by dissolving 5.58 g of gadolinium chloride hexahydrate in 500 ml of anhydrous diethylene glycol (DEG) at ambient temperature. A second solution of 500 ml of PEG containing 4.95 ml of 10 M sodium hydroxide is added to the first solution. The addition takes place at ambient temperature over the course of 24 H. A transparent colloidal solution is obtained with a mean size for the oxide cores of 3.5 nm in diameter (measurements obtained by PCS and by TEM microscopy).

Encapsulation

The growth of the polysiloxane layer is provided via a sol-gel reaction by adding two silane precursors (APTES and TEOS) in a 60/40 proportion and triethylamine as catalyst. To do this, 1050 μl of APTES and 670 μl of TEOS are added to the previous solution with vigorous stirring at 40° C. For the purpose of obtaining fluorescence in the near-IR, a variable amount of APTES can be coupled to Cy5.5 mono-NHS-ester by creating an amide bond between the APTES and the fluorophore. After 1 H of reaction, 2550 μl of a solution of DEG containing triethylamine (0.1 M of TEA, 10 M of water) are added. The sol-gel reaction previously described is repeated three times, each time 24 H apart. At the end of these various steps, the solution is left to stir at 40° C. for 48 H. The final colloidal solution exhibits particles with a mean size of 4.5 nm.

Surface Functionalization

Finally, a considerable excess of DOTAGA (2 DOTAGA per Gd atom) is added to the particles, allowing the formation of a peptide bond between the available amine functions of the surface and a carboxylic acid function of the ligand. 13.76 g of DOTAGA are dispersed in 200 ml of DMSO. After the addition of the particle solution to the solution containing DOTAGA, the mixture is left to stir for a further 48 hours. The nanoparticles are then precipitated from 9 l of acetone. The acetone is removed and the particles are washed with a further 3 l of acetone and recovered by centrifugation. The particles are then redispersed in 200 ml of distilled water, the excess of acetone is evaporated off and then the solution is kept stirring for a further 24 h. The purification is carried out by tangential centrifugation through Vivaspin® membranes (pore size: 5 kDa). Finally, the resulting purified solutions are lyophilized and then stored in a refrigerator for several months without modification of the product. In order to obtain particles which are more fluorescent, it is also possible to add the Cy5.5 post-grafting, i.e. after the particles have been obtained, by direct reaction of the Cy5.5 mono-NHS-ester with the free amine functions of the particle. The fluorescence analysis of the particles made it possible to demonstrate that it is possible to graft approximately one Cy5.5 per particle. The size of these nanoparticles was obtained by fluorescence correlation spectroscopy and made it possible to obtain a hydrodynamic diameter of 4 nm slightly larger than that obtained without fluorophore.

The nanoparticles without fluorophore have a hydrodynamic radius of 3±0.1 nm once rediluted in aqueous solution. The weight of the particles was estimated at 8.5±1 kDa according to a mass spectrometry analysts. The longitudinal relaxivity $r_1$ is 11.4 mmol$^{-1}$ s$^{-1}$ at 60 MHz. At high field (300 MHz), the relativity obtained at 300 MHz is 6 mmol$^{-1}$ s$^{-1}$. The elemental analysis combined with the particle size makes it possible to obtain a total of 10 DOTA, 27 Si and 7 Gd per particle. These data were corroborated by a potentiometric and fluorescence assay of a number of free DOTAs present per particle. Before the use of the particles for the biological applications, the free DOTAs are used to chelate other Gd$^{3+}$ ions in order to maximize the $r_1$ per object (114 mmol$^{-1}$·s$^{-1}$ per object on average) or to chelate active ions in SPECT or PET scintigraphy. This method is described in the literature (Lux et al., *Ange. Chem. Int. Ed.*, 2011, 50, 12299). A solution for injection of these nanoparticles is prepared by dilating the particles in a saline solution with a HEPES buffer in order to fix the pH. An intravenous injection in the tail of rodents (rats or mice) made it possible to show elimination of the particles via the kidneys, combined with a plasma lifetime twice as long as DOTAREM®.

Example 2

Functionalization of the Nanoparticles for Active Targeting of Tumors: SRP-cRGD

The nanoparticles used for the grafting are similar to those described in example 1. They therefore possess a set of free DOTAs (and thus of available carboxylic acid functions) for the grafting of cRGD which is known to be an agent that targets $\alpha_v\beta_3$ integrin. The grafting of cRGD to the particle is carried out by means of peptide coupling between a carboxylic acid function of a DOTA unit and the primary amine function of the cRGD peptide. The nanoparticles obtained in example 1 are diluted in water ($Gd^{3+}$ concentration of around 100 mM). A mixture of EDC and NHS (3.4 EDC and 3.4 NHS per Gd) is added to the particles, the pH is adjusted to 5 and the mixture is kept stirring for 30 minutes. The cRGD (2.3 cRGD per Gd) is dissolved separately in anhydrous DMSO. It is then added to the previous solution and the pH of the mixture is adjusted to 7.1 before leaving it to stir for 8 hours. The solution is finally purified by tangential filtration through a 3 kDa membrane, before being lyophilized. The elemental analysis makes it possible to work back to a cRGD content of approximately 2.5 per particle. The same protocol is used to graft cRAD to the nanoparticles; these nanoparticles will serve as a control in the active targeting tests carried out with cRGD.

Example 3

Analysis of the Interaction of SRPcRGD Nanoparticles Obtained According to Example 2 with Cells Expressing $\alpha v\beta 3$ Integrin by Flow Cytometry and Fluorescence Microscopy Analysis by Fluorescence Microscopy HEK293($\beta$3) cells, which overexpress $\alpha_v\beta_3$ integrin, are cultured on coverslips in 12-well plates (100 000 cells per well) overnight at 37° C. They are rinsed once with 1×PBS, then with 1×PBS containing 1 mM of $CaCl_2$ and 1 mM of $MgCl_2$. They are then incubated for 30 minutes at 4° C. (binding analysis) or 30 minutes at 37° C. (internalization analysis), in the presence of SRP (nanoparticles according to example 1) with a fluorophore of Cy5.5 type, of SRP-cRGD (obtained according to example 2) Cy5.5 or of SRP-cRAD (obtained according to example 2 and acting as a negative control) Cy5.5 at a $Gd^{3+}$ ion concentration of 0.1 mM. They are then rinsed with PBS $Ca^{2+}/Mg^{2+}$ (1 mM) and fixed (10 minutes with 0.5% paraformaldehyde. The nuclei are labeled with Hoechst 33342 (5 µM for 10 minutes) (Sigma Aldrich, Saint Quentin Fallavier, France). After washing with 1×PBS, the coverslips are mounted with Mowiol. The images are taken with an Apotome microscope (Carl Zeiss, Jena, Germany).

Analysis by Flow Cytometry

Before the binding analysis, the adherent cells (HEK293 ($\beta$3)) are trypsinized, then rinsed once with cold (4° C.) 1×PBS, and a second time with cold 1×PBS $Ca^{2+}/Mg^{2+}$ (1 mM). One million cells, in a final volume of 200 µl, are resuspended in a solution of SRP Cy5.5, of SRP-RGD Cy5.5 or of SRP-RAD Cy5.5 at a $Gd^{3+}$ ion concentration of 0.1 mM and incubated for 30 minutes at 4° C. After two rinses with PBS $Ca^{2+}/Mg^{2+}$ (1 mM), the cells are rapidly analyzed by flow cytometry (LSR II, Becton Dickinson, France).

For the internalization analysis, the protocol is similar, with reagents at 37° C. and an incubation for 30 minutes at 37° C.

The results obtained, by flow cytometry and by microscopy, made it possible to demonstrate specific binding and internalization of the SRP-RGD Cy5.5 on the HEK293($\beta$3) cells, which binding is not observed with the SRP Cy5.5 and the SRP-RAD Cy5.5 (results not shown).

Example 4

MRI Imaging of the Lung Using SRP Nanoparticles Synthesized According to Example 3

A concentration study was carried out in order to determine the injection concentration most suitable for observing the best MRI contrast. The mice were anesthetized by virtue of an intraperitoneal injection by means of 50 µg/g of ketamine (Panpharma, France) and 5 µg/g of xylazine (Sigma-Aldrich, Saint-Quentin Fallavier, France). After the image acquisition without contrast agent, the mice were incubated intratracheally by means of a 22-gauge intravenous Teflon catheter. A volume of 50 µl of the SRP solution was introduced into the lungs by the catheter. 7 different $Gd^{3+}$ concentrations were tested (2, 5, 10, 20, 33, 50 and 100 mM), while a saline solution was injected into a control mouse. Once the intubation was stopped, the lung image acquisition was carried out at regular intervals over a period of between 5 minutes and several hours after the instillation of the solution. Among all these concentrations, it is the 50 mM concentration which exhibited the best signal enhancement (235±15%), the signal enhancement being a little less in the case of the 100 mM concentration (171±10%). The signal enhancement is defined as the difference between the signal-to-noise ratio in the lungs before and after the administration, normalized with respect to the signal-to-noise ratio in the lungs before the administration of the contrast agent.

The 50 mM concentration was therefore retained for carrying out the subsequent biodistribution studies by MRI. Another study was carried out using this optimum concentration of 50 mM on 3 mice. For these animals, the MRI imaging of the lungs, of the liver, of the kidneys and of the bladder was carried out at regular intervals between 5 minutes and 2 days after the administration of the contrast agent. These manipulations made it possible to demonstrate that the half-lifetime of the contrast agent excreted by the kidneys is 149±51 minutes. This elimination of the nanoparticles by the kidneys is due to their small size and represents a real advantage in terms of toxicity of the contrast agent. It will also be important for an original application described in example 10.

Example 5

2D and 3D Fluorescence and X-Ray Imaging of the Lung Using SRP Nanoparticles Synthesized According to Example 1

The lyophilized SRP Cy5.5 obtained according to example 1 are solublized in an appropriate volume of water to obtain an injectable preparation for at least 30 minutes, in order to obtain a solution at 100 mM with respect to $Gd^{3+}$ ions. The suspension of particles is then diluted in a solution containing a HEPES buffer and a saline solution. The preparation obtained has a pH of 7.4 and an osmolarity suitable for administration to animals.

The intrapulmonary nebulization is carried out using a Microsprayer® (PennCentury®). Each mouse is anesthetized (Domitor/Ketamine mixture, intrapertioneal injection) and receives 50 µl of nanoparticulate suspension via the intrapulmonary route. The mice used for the proof of concept by fluorescence imaging are 6-week-old NMRI nude mice weighing approximately 25 grams (Janvier, Le Genest Saint Isle, France).

The results obtained by 2D and 3D fluorescence and X-ray imaging showed a distribution of the fluorescent nanoparticles in the two lungs after nebulization. These results presented in FIG. 1 are in perfect agreement with those obtained by MRI.

Example 6

Synthesis of Nanoparticles for Radiosensitizing Effect on Lung Tumors

This example describes the synthesis of nanoparticles employed for use as a radiosensitizing agent in the context of glioblastoma treatment (G. Le Duc et al., *ACS Nano*, 2011, 5, 9566). These nanoparticles are gadolinium oxide nanoparticles covered with a layer of polysiloxane functionalized with DTPA (complex also chelating a gadolinium ion). They are envisioned for treatment of pulmonary tumors by radiosensitization owing to their characteristics which are very similar to the nanoparticles described in example 1 (both in terms of size and in terms of morphology).

The synthesis of the gadolinium oxide core is carried out by dissolving the gadolinium chloride hexahydrate salt (5.576 g) in 100 ml of DEG at ambient temperature and with vigorous stirring. The suspension is healed at 140° C. until complete dissolution of the salt (approximately 1 hour). When the solution has become clear, sodium hydroxide (4 ml, 3.38 M) is added dropwise to the solution while maintaining vigorous stirring. At the end of this addition, the stirring and the heating are maintained for 3 hours. A transparent colloidal solution of gadolinium oxide cores is then obtained, which can be stored at ambient temperature for several weeks without modification.

The functionalization with the polysiloxane layer is carried out in the presence of the silane precursors (APTES (10.1 ml) and TEOS (6.4 ml)) and of a hydrolysis solution (triethylamine in DEG (0.1 M of TEA and 10 M of water)). The solutions are added in several steps to 400 ml of the solution previously prepared containing the gadolinium oxide cores ($[Gd^{3+}]$=45 mM) with stirring at 40° C. A silicon content 4 times greater than the gadolinium content is chosen for this synthesis (the precursor mixture is composed of 60% of APTES and 40% of TEOS). The addition of the various precursors is carried out in 6 successive steps. Each step consists of the addition of a part of the solution containing the precursor mixture (5% of the solution for the first step, 15% for the second and 20% for the subsequent steps). The delay between each addition is set at 1 hour. After the final addition, the solution is left to stir for 48 hours at 40° C.

In order to facilitate their colloidal stability in a biological medium, the nanoparticles are functionalized with DTDTPA by virtue of a peptide bond between one of the activated carboxylic acid functions and an amine function resulting from the APTES present at the surface of the nanoparticles. 100 ml of the colloidal solution of nanoparticles previously obtained are added to 4.25 g of DTDTPA dissolved in 20 ml of DMSO.

The nanoparticles are then precipitated from 500 ml of acetone and the supernatant is removed by centrifugation. The white powder obtained is then washed with an ethanol/acetone (85/15) mixture and the supernatant is again removed by centrifugation (the operation is repeated 3 times). The nanoparticles are then dispersed in water and purified by tangential centrifugation (through Vivaspin® 5 kDa membranes).

After a purification by a factor of 1000, the particles are lyophilized. They are then directly injectable by virtue of a HEPES buffer and a saline solution at the correct osmolarity, the pH being adjusted to 7.4. These nanoparticles have a hydrodynamic diameter of 2 nm and an $r_1$ at 60 MHz of 9.4 $mM^{-1} \cdot s^{-1}$ (the $r_1$ to $r_2$ ratio is 1.13). They can therefore be used as $T_1$ contrast agents in order to visualize their biodistribution and their accumulation in the tumor (G. Le Duc et al., *ACS Nano*, 2011, 5, 9566). This monitoring by imaging is important in order to determine the optimum time at which to initiate the radiotherapy. These therapeutic agents have already proved their radiosensitizing capacity in vitro on human brain cancer cells of U87 type (P. Mowat et al., *Journal of Nanoscience and Nanotechnology*, 2011, 11, 7833-7839). The use of these nanoparticles or else of those described in examples 1 and 2 therefore appears to be particularly suitable in the context of combating lung cancer by carrying out imaging-guided therapy (in this case radiotherapy).

Example 7

Protocol Envisioned for a Radiosensitization Application of these Nanoparticles Injected Via the Airways The nanoparticles synthesized according to example 1 are injected via the airways. Their accumulation in the tumor zone is then pinpointed by means of MRI (example 4), of florescence imaging coupled to X-ray tomography (example 5) or else of scintigraphy after chelation of a radioactive isotope used in PET or in SPECT. Once the nanoparticle concentration is pinpointed as optimal in the tumor zone (ratio of the contrast between the healthy zone and the tumor zone), the treatment by radiotherapy can be activated. The nanoparticles are subsequently eliminated by the kidneys after they have passed into the blood. The administration via the airways makes it possible to inject a smaller amount of nanoparticles into the patient. Since treatment by radiotherapy is divided up into sessions under clinical conditions, it will then be possible to carry out a further administration of particles before each of these sessions because of the possibility of elimination of these particles and the relatively small amounts injected. The various trials previously carried out on radioresistant tumors of U87 type lead one to predict advantageous results in lung radiosensitization.

Example 8

Theranostic for Asthma

No noninvasive imaging technique currently makes it possible to evaluate the severity and the extent of bronchial remodeling in severe asthmatics. Bronchial remodeling corresponds to an abnormal change in the bronchial and peribronchial tissues following repeated bronchial inflammation. This remodeling results in various histological changes: thickening of the subepithelial membrane, increase in extracellular matrix deposits, neoangiogenesis, mucus gland hypertrophy and increase in bronchial smooth muscle mass. Bronchial remodeling in severe asthmatics results in an unfavorable prognosis, significant morbidity and a marked degradation of respiratory function; furthermore, patients do not respond to the usual therapies. Severe asthmatics represent 10% of the asthmatic population, i.e. 350 000 patients in France, and more than half the costs associated with this pathological condition. For the development of effective treatments, it is essential to have available a noninvasive imaging technique which makes it possible to accurately evaluate the severity of the remodeling and the response to treatments. The use of aerosols of nanoparticles grafted with targeting molecules (for example the cRGD tripeptide for αvβ3 integrin as described in example 2) should allow the imaging of the angiogenesis associated with bronchial remodeling for the diagnosis and for the evaluation of the therapeutic efficacy of the treatment of severe asthma. With this objective, it will be possible to set up a murin modeling of chronic asthma. These mice (6-week-old female Balb/c mice) will receive intraperitoneal injections of ovalbumin (100 μg) or of *Dermatophagoides pteronyssinus* (*D. pter*) (100 μg) for sensitization and then intranasal instillations of the same compounds at regular intervals (days 14, 27, 28, 29, 47, 61, 73, 74 and 75) for the appearance of bronchial remodeling 15 weeks after the beginning of the sensitization.

Example 9

Synthesis of Nanoparticles for Dynamic Phototherapy Effect on Lung Tumors

The addition of a photosensitizer to the nanoparticles makes it possible to give them a toxic effect under the action of light. Nevertheless, light cannot penetrate into the body beyond a few centimeters, even with the most appropriate chromophores (absorption in the tissue transparency window, i.e. the near-infrared zone). The main advantage of the approach via the airways is to be able to obtain a concentration in pulmonary tumors. The latter can then be illuminated by means of the optical fiber of an endoscope (thus avoiding the problems of penetration of the tissues by light).

The synthesis of nanoparticles which have an action by PDT and which can be injected via the airways is set up in the following way:

Gadolinium chloride hexahydrate (3.346 g) is placed in 60 ml of DEG at ambient temperature. The suspension is then heated at 140° C. with vigorous stirring in order to ensure total dissolution of the gadolinium salt. 4 ml of a 2.03 M sodium hydroxide solution are then added dropwise while maintaining the vigorous stirring. The solution is then left to stir at 180° C. for 3 hours. A colloidal solution of gadolinium oxide cores is then obtained, which can be stored at ambient temperature for several weeks without risk of degradation.

The addition of a chlorine-derived photosensitizer (TPC) can be carried out by virtue of the activation of the carboxylic acid function of the TPC with an EDC/NHS mixture so as to obtain the 5,10,15-tri-(p-tolyl)-20-(p-carboxylphenyl) chlorinesuccinidyl ester (TPC-NHS) according to the protocol described by C. Frochot et al. (*Bioorganic Chemistry*, 2007, 35, 205-220). 20 mg of TPC-NHS are coupled by peptide bonding with 12.3 μl of APTES in 4.2 ml of anhydrous DMSO overnight.

The silane precursors (APTES (1.5 ml) and TEOS (1.0 ml)) and also the hydrolysis solution (aqueous solution of triethylamine in DEG (0.015 M of TEA and 1.5 M of water)) are added stepwise to the 60 ml of DEG containing the particles, with stirring at 40° C. The total addition is carried out in 6 steps. Each step consists of the addition of a part of the precursor solution to the colloidal solution in PEG (5% for the first step, 15% for the next step and 20% for the final steps). The solution containing the TPC coupled to the APTES is added during the first step at the same time as the other precursors. The time between each addition is one hour. After the final addition, the mixture is kept stirring for 48 hours at 40° C.

The nanoparticles are then functionalized with DTDTPA by means of peptide coupling between the amines of the APTES and the activated carboxylic acid function of the completing agent, 2.5 g of DTDTPA in 12 ml of anhydrous DMSO are added to the previous solution. The resulting mixture is their stirred for 1 hour. The nanoparticles are then precipitated from 300 ml of acetone and the supernatant is removed by centrifugation. The powder obtained is washed 3 times with an ethanol/acetone (85/15) mixture. The powder is finally redispersed in water and purified by tangential centrifugation on a 5 kDa membrane (Vivaspin®). This procedure is repeated several times in order for a degree of purification of at least 100 to be reached. The purified solution of colloids is then lyophilized.

Example 10

Passive Targeting of a Subcutaneous Tumor After Intrapulmonary Administration of Nanoparticles The lyophilized cyanine 5.5 particles are solubilized in an appropriate volume of injection-grade water for at least 30 minutes, in order to obtain a solution at 100 mM with respect to $Gd^{3+}$ ions. The suspension of particles is then diluted in a solution containing a HEPES buffer and a saline solution. The preparation obtained has a pH of 7.4 and an osmolarity which is suitable for administration to animals.

The mice received, beforehand, a subcutaneous graft of tumor cells on the flank. When the tumor reaches a size of 5×5 mm, the mice receive an intrapulmonary injection of nanoparticles (50 μL per mice). The nebulization is carried out using a Microsprayer® (Penncentury®).

The results obtained showed a very rapid passage of the particles into the blood stream (15-20 minutes) from the lungs, combined with elimination via the kidneys.

A signal is detected in the subcutaneous tumor starting from 5 h after the nebulization. The signal increases up to 24 h alter the administration.

Figure 5:
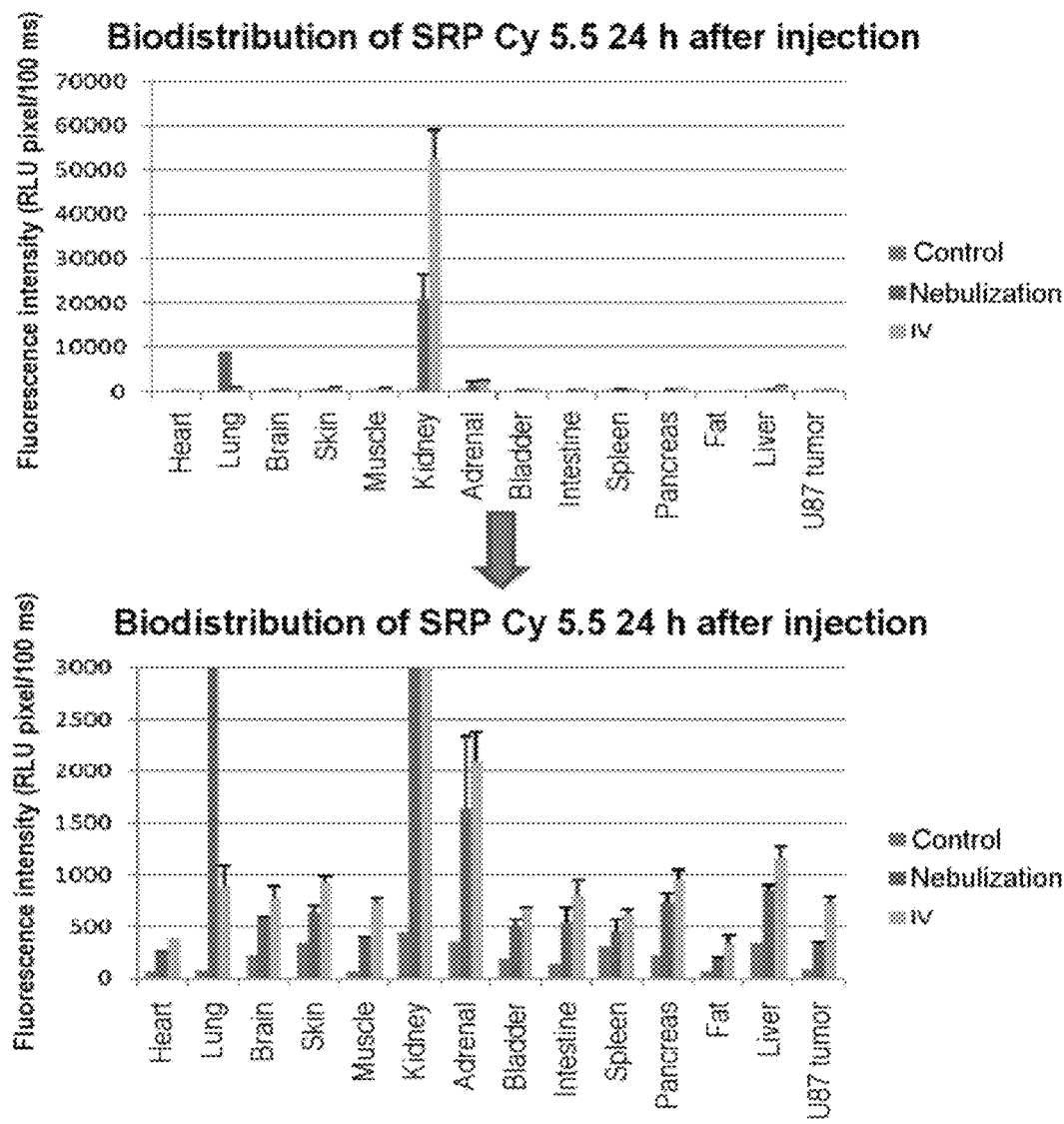
FIG. 5: biodistribution of the SRP Cy 5.5 24 h after intrapulmonary nebulization or intravenous injection of a suspension of particles at 10 mM with respect to $Gd^{3+}$ ions. The nanoparticles are obtained according to example 1 with coupling of a fluorophore of Cy 5.5 type to the nanoparticle.

The biodistribution is comparable to that obtained for the administration of an equivalent amount of $Gd^{3+}$ ions intravenously (injection in the caudal vein), but with a slightly lower passive tumor accumulation (FIG. 5). The nanoparticles injected via the airways have the advantage of ensuring a lower renal uptake.

Example 11

Passive Targeting of an Orthotopic Pulmonary Tumor After Intravenous or Intrapulmonary Administration of Nanoparticles The lyophilized cyanine 5.5 particles are solubilized in as appropriate volume of injection-grade water for at least 30 minutes, in order to obtain a solution at 100 mM with respect to $Gd^{3+}$ ions. The suspension of particles is then diluted in a solution containing a HEPES buffer and a saline solution. The preparation obtained has a pH of 7.4 and an osmolarity appropriate for administration to animals.

The mice received, beforehand, an orthotopic graft of pulmonary tumor cells (H358) in the lung. The tumor cells stably express the luciferase gene, thereby making it possible to monitor the tumor growth by bioluminescence imaging in vivo. When the tumor is well established and detectable by bioluminescence imaging in vivo, the mice receive an intravenous injection (200 μl per mouse) or an intrapulmonary injection (50 μl per mouse) of nanoparticles. The nebulization is carried out using a Microsprayer® (Penncentury®).

The results obtained show that, after intravenous administration, the particles are distributed throughout the body of the mouse and are eliminated via the kidneys. Starting from 5 h after the administration, a signal is detectable by 3D fluorescence imaging in the H358 pulmonary tumor implanted orthotopically in the lung. The signal is stable up to 24 h post-administration.

As regards the intrapulmonary administration, the results show that, after administration, the particles pass very rapidly into the blood stream (15-20 minutes) from the lungs, and are eliminated via the kidneys. Starting from 5 h after the nebulization, most of the particles are eliminated from the lung and a signal is detectable in the pulmonary tumor orthotopically implanted in the lung. The signal is stable up to 24 h post-administration.

Figure 6:
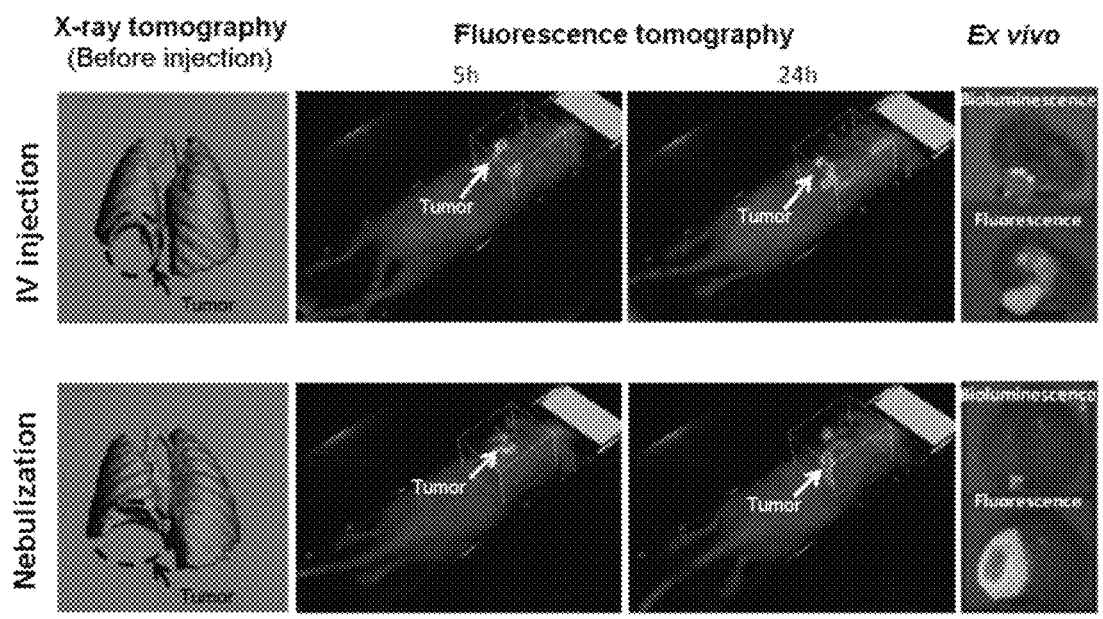
FIG. 6: passive targeting of orthotopic H358-Luc pulmonary tumors after intravenous injection or intrapulmonary nebulization of a suspension of nanoparticles. The nanoparticles are obtained according to example 1 with coupling of a fluorophore of Cy 5.5 type to the nanoparticle.

The in vivo fluorescence imagings show good colocalization of the fluorescence with the presence of the tumor (X-ray tomography carried out before the administration of the particles, see FIG. 6).

The fluorescence and bioluminescence imagings carried out ex vivo on the lungs show a colocalization of the bioluminescence signal (corresponding to the turner cells) and of the fluorescence (corresponding to the Cy5.5-particles) (see FIG. 6).

The particles are therefore capable of passively accumulating in orthotopically implanted pulmonary tumors, irrespective of the route of administration (intravenous or intrapulmonary).

Example 12

Radiosensitizing Effect of the Nanoparticles on Pulmonary Tumors After Intrapulmonary Administration The lyophilized particles are solubilized in an appropriate volume of injection-grade water for at least 30 minutes. In order to obtain a solution at 100 mM with respect to $Gd^{3+}$ ions. The suspension of particles is then diluted in a solution containing a HEPES buffer and a saline solution. The preparation obtained has a pH of 7.4 and an osmolarity appropriate for administration to animals.

The mice received, beforehand, an orthotopic graft of pulmonary tumor cells (H358) in the lung. The tumor cells stably express the luciferase gene, thereby making it possible to monitor the tumor growth by bioluminescence imaging in vivo. When the tumor is well established and detectable by bioluminescence imaging in vivo, the mice receive an intrapulmonary injection (50 μl per mouse) of nanoparticles. The nebulization is carried out using a Microsprayer® (Penncentury®). Twenty-four hours post-administration, the mice are irradiated (X-rays) in a single dose in a conventional irradiator.

Figure 7:
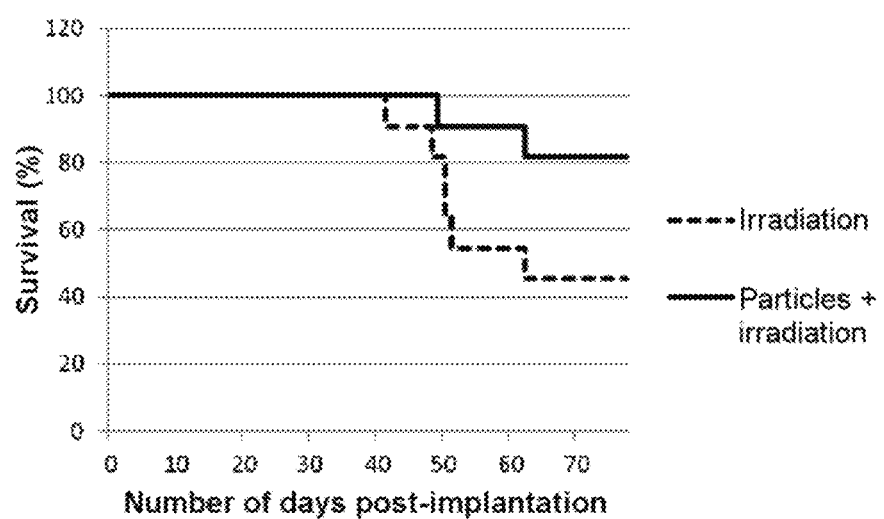
FIG. 7: survival curves (Kaplan-Meier) obtained on mice carrying H358 orthotopic pulmonary tumors, treated by 10 Gy irradiation alone or treated by 10 Gy irradiation carried out 24 h after intrapulmonary administration of a suspension of nanoparticles at 20 mM with respect to $Gd^{3+}$ ions.

The results obtained show that the intrapulmonary administration of the nanoparticles before irradiation improves the survival of the mice, in comparison with a single irradiation (see FIG. 7). The particles therefore exhibit a radiosensitizing effect for the pulmonary tumors.

The invention claimed is:

1. A method for imaging or treating a lung tumor in a subject in need thereof, comprising
   administering via the subject's airways, an effective amount of ultrafine nanoparticles as an imaging agent for imaging a tumor that is located in said subject's lungs, as a radiosensitizing agent for treating a tumor that is located in said subject's lungs, or both, said ultrafine nanoparticles having the following properties:
   said ultrafine nanoparticles comprise a polyorganosiloxane matrix;
   said ultrafine nanoparticles also comprise a chelating agent complexing cations $M^{n+}$, M being a rare earth metal, n being an integer between 2 and 4, and optionally doping cations $D^{m+}$, D being a rare earth metal other than M, an actinide or a transition element, m being an integer between 2 and 6, and
   said ultrafine nanoparticles have a mean diameter having been reduced to a value between 1 and 5 nm by dissolution of all or part of a precursor nanoparticle comprising a core made of a metal oxide or oxyhydroxide of M, and,
   irradiating said subject, imaging said subject or both.

2. The method of claim 1, wherein said ultrafine nanoparticles comprise at least one imaging agent for $T_1$ MRI imaging, and at least one imaging agent suitable for one of the following imaging techniques:
   (i) PET or SPECT scintigraphy,
   (ii) fluorescence in the near-infrared range, and
   (iii) X-ray tomodensitometry.

3. The method of claim 1, wherein said $M^{n+}$ is $Gd^{3+}$ and said ultrafine nanoparticles have a relaxivity r1 per ultrafine nanoparticle of between 50 and 5000 $mM^{-1} \cdot s^{-1}$ at 1.4 T.

4. The method of claim 1, wherein M is a lanthanide.

5. The method of claim 4, wherein said lanthanide is selected from the group consisting of Dy, Lu, Gd, Ho, Eu, Tb, Nd, Er, Yb and mixtures thereof.

6. The method of claim 1, wherein each ultrafine nanoparticle is obtained from a precursor nanoparticle comprising:
   a core comprising a metal oxide or oxyhydroxide of M, at least partly in cationic form $M^{n+}$, n being an integer between 2 and 4, optionally doped with a doping agent D present at least partly in cationic form $D^{m+}$, m being an integer between 2 and 6;
   at least one coating layer comprising polyorganosiloxanes (POSs);
   and, optionally, an overcoating comprising a chelating agent C1 capable of complexing the $M^{n+}$ cations or a hydrophilic molecule capable of suspending the precursor nanoparticle in an aqueous medium;
   said precursor nanoparticle having been subjected to dissolution of the core using a pH-modifying agent or a chelating agent C2, identical to or different than C1, capable of complexing all or part of the $M^{n+}$ and $D^{m+}$ cations, such that a mean diameter of the ultrafine nanoparticle thus obtained is reduced to a value of between 1 and 5 nm.

7. The method of claim 1, wherein said ultrafine nanoparticles further comprise a radioactive isotope that can be used in scintigraphy.

8. The method of claim 7, wherein said radioactive isotope is a radioactive isotope of In, Tc, Ga, Zr, Y, Cu or Lu.

9. The method of claim 7, wherein said radioactive isotope is selected from the group consisting of $^{111}$In, $^{99m}$Tc, $^{68}$Ga, $^{64}$Cu, $^{89}$Zr, $^{90}$Y and $^{177}$Lu.

10. The method of claim 1, wherein said ultrafine nanoparticles comprise a $T_1$ contrast agent suitable for magnetic resonance imaging.

11. The method of claim 1, wherein the ultrafine nanoparticles comprise a multimodal contrast agent suitable for $T_1$ MRI imaging, and at least one imaging technique chosen from the group consisting of:
   i. PET or SPECT scintigraphy,
   ii. fluorescence in the near-infrared range, and
   iii. X-ray tomodensitometry.

12. The method of claim 1, wherein said ultrafine nanoparticles have a Gd weight ratio between 5% and 50%.

13. The method of claim 1, wherein said chelating agent is selected from the group consisting of diethylenetriaminepentaacetic acid (DTPA), 1,4,7,10-tetraazacyclododecane-1,4,7,10-tetraacetic acid (DOTA), 1,4,7-triazacyclononane-1,4,7-triacetic acid (NOTA), and derivatives thereof.

14. The method of claim 1, wherein said ultrafine nanoparticles are administered intranasally or intratracheally.

15. The method of claim 1, wherein said ultrafine nanoparticles are used both as an imaging agent for MRI of tumors and as a radiosensitizing agent for treating said tumors.

16. A noninvasive method of imaging of a lung tumor in a human patient or an animal patient, comprising the following steps:
   (i) administering to said human or animal patient, via the human or animal patient's airways, an effective amount of ultrafine nanoparticles having the following properties:
      said ultrafine nanoparticles comprise a polyorganosiloxane matrix;
      said ultrafine nanoparticles comprise a chelating agent complexing cations $M^{n+}$, M being a rare earth metal, n being an integer between 2 and 4, and optionally doping cations $D^{m+}$, D being a rare earth metal other than M, an actinide or a transition element, m being an integer between 2 and 6; and
      said ultrafine nanoparticles have a mean diameter having been reduced to a value between 1 and 5 nm by dissolution of all or a part of a precursor nanoparticle comprising a core made of a metal oxide or oxyhydroxide of M; and,
   (ii) capturing MRI images using an appropriate MRI sequence, wherein said tumor is located in said human or animal patient's lungs.

17. The method of claim 16, wherein the ultrafine nanoparticles are administered in the form of an aerosol.

18. A method for monitoring the therapeutic efficacy of a therapeutic treatment of a lung tumor in a human or animal, said method comprising the following steps:
   (i) at the initiation of a treatment of a human or animal, administering an effective amount of ultrafine nanoparticles as an imaging agent, said ultrafine nanoparticles having the following properties:
      said ultrafine nanoparticles comprise a polyorganosiloxane matrix,
      said ultrafine nanoparticles also comprise a chelating agent complexing cations $M^{n+}$, M being a rare earth metal, n being an integer between 2 and 4, and optionally doping cations $D^{m+}$, D being a rare earth metal other than M, an actinide or a transition element, m being an integer between 2 and 6, and
      said ultrafine nanoparticles have a mean diameter having been reduced to a value between 1 and 5 nm by dissolution of all or part of a precursor nanoparticle comprising a core made of a metal oxide or oxyhydroxide of M,
   (ii) capturing images of the imaging agent using an appropriate imaging technique in order to visualize the tumor, said tumor being located in the lungs of said human or animal,
   (iii) repeating steps (i) and (ii) during the treatment of the human or animal, and
   (iv) comparing the change in said tumor during the treatment, thereby deducing the therapeutic efficacy of the treatment.

* * * * *